United States Patent [19]

MacDonald et al.

[11] Patent Number: 5,366,889
[45] Date of Patent: Nov. 22, 1994

[54] DNA ENCODING A PROTEIN-COUPLED RECEPTOR KINASE

[75] Inventors: Marcy E. MacDonald, Lexington; James F. Gusella, Framingham; Christine Ambrose, Charlestown, all of Mass.

[73] Assignee: The General Hospital Corporation, Boston, Mass.

[21] Appl. No.: 980,526

[22] Filed: Nov. 30, 1992

[51] Int. Cl.$^5$ ............... C12N 15/12; C12N 15/63
[52] U.S. Cl. ................ 435/252.3; 435/69.1; 435/370.1; 435/6; 536/23.2
[58] Field of Search ............... 536/23.5; 435/6, 69.1, 435/202.3, 370.1

[56] References Cited

U.S. PATENT DOCUMENTS 4,666,828  5/1987  Gusella ............................. 435/6

OTHER PUBLICATIONS

P.N.A.S. 90:5588–92 (Jun. 1993) Kunapwli et al. Cloning and expression of GRK5: A member of the G protein–coupled reception Kiwase fault.

Allitto, Bernice A. et al., "Increased Recombination Adjacent to the Huntington Disease–Linked D4S10 Marker", *Genomics* 9:104–112 (1991).

Altschul, Stephen F. et al., "Basic Local Alignment Search Tool," *J. Mol. Biol.* 215:403–410 (1990).

Barron, Lilias et al., "Linkage Disequilibrium and Recombination Make a Telomeric Site for the Huntington's Disease Gene Unlikely", *J. Med. Genet.* 28:520–522 (1991).

Bates, G. P. et al., "Defined Physical Limits of the Huntington Disease Gene Candidate Region", *Am. J. Hum. Genet.* 49:7–16 (1991).

Benovic, Jeffrey L. et al., "β–Adrenergic Receptor Kinase: Identification of a Novel Protein Kinase That Phosphorylates the Agonist–Occupied Form of the Receptor", *PNAS–USA* 83:2797–2801 (May 1986).

Benovic, Jeffrey L. et al., "Regulation of Adenylyl Cyclase–Coupled β–Adrenergic Receptors", *Ann. Rev. Cell Biol.* 4:405–428 (1988).

Benovic, Jeffrey L. et al., "Purification and Characterization of the β–Adrenergic Receptor Kinase", *The Journal of Biological Chemistry* 262(19):9026–9032 (1987).

Benovic, Jeffrey L. et al., "cDNA Cloning and Chromosomal Localization of the Human β–Adrenergic Receptor Kinase", *FEBS* 283(1):122–126 (May 1991).

Benovic, Jeffrey L. et al., "Cloning, Expression, and Chromosomal Localization of β–Adrenergic Receptor Kinase 2", *The Journal of Biological Chemistry* 266(23):14939–14946 (Aug. 15, 1991).

Benovic, Jeffrey L. et al., "β–Adrenergic Receptor Kinase: Primary Structure Delineates a Multigene Family", *Science* 246:235–240 (Oct. 13, 1989).

Buckler, Alan J. et al, "Exon Amplification: A Strategy to Isolate Mammalian Genes Based on RNA Splicing", *PNAS–USA* 88:4005–4009 (May 1991).

Cassill, J. Aaron et al., "Isolation of Drosphila Genes Encoding G Protein–Coupled Receptor Kinases", *PNAS–USA* 88:11067–11070 (Dec. 1991).

Devereux, John et al., "A Comprehensive Set of Sequence Analysis Programs for the VAX", *Nucleic Acids Research* 12(1):387–395 (1984).

Gilliam, T. Conrad et al., "Localization of the Huntington's Disease Gene to a Small Segment of (List continued on next page.)

Primary Examiner—Robert J. Hill, Jr.
Assistant Examiner—John D. Ulm
Attorney, Agent, or Firm—Sterne, Kessler, Goldstein & Fox

[57] ABSTRACT

This invention relates to a DNA segment which encodes at least one member of the family of mammalian G protein-coupled receptor kinases, which maps to the Huntington's disease region within the terminal cytogenic subband of the short arm of chromosome 4, 4p16.3, between DNA marker D4S10 and the telomere region. Further, this invention provides the substantially purified expression product of a gene from the Huntington's disease region of the chromosome, as well as related diagnostic and therapeutic uses.

11 Claims, 4 Drawing Sheets

OTHER PUBLICATIONS

Chromosome 4 Flanked by D4S10 and the Telomere", *Cell* 50:565–571 (Aug. 14, 1987).

Gusella, James F. et al., "A Polymorphic DNA Marker Genetically Linked to Huntingtons's Disease", *Nature* 306:234–238 (1983).

Gusella, James F. et al., "DNA Markers for Nervous System Diseases", *Science* 225:1320–1326 (Sep. 21, 1984).

Gusella, James F., "Huntington's Disease", *Advances In Human Genetics*, vol. 20, pp. 125–151 (1991).

Lin, Carol S., "New DNA Markers in the Huntington's Disease Gene Candidate Region", *Somatic Cell and Molecular Genetics* 17(5):481–488 (1991).

Lorenz, Wulfing et al., "The Receptor Kinase Family: Primary Structure of Rhodopsin Kinase Reveals Similarities to the β–Adrenergic Receptor Kinase", *PNAS-USA* 88:8715–8719 (Oct. 1991).

MacDonald, Marcy E. et al., "A Somatic Cell Hybrid Panel for Localizing DNA Segments Near the Huntington's Disease Gene", *Genomics* 1:29–34 (1987).

MacDonald, Marcy E. et al., "The Huntington's Disease Candidate Region Exhibits Many Different Haplotypes", *Nature Genetics* 1:99–103 (May 1992).

MacDonald, Marcy E. et al., "Recombination Events Suggest Potential Sites for the Huntington's Disease Gene", *Neuron* 3:183–190 (Aug. 1989).

MacDonald, Marcy E. et al., "Complex Patterns of Linkage Disequalibrium in the Huntington Disease Region", *Am. J. Hum. Genet.* 49:723–734 (1991).

Marchuk, Douglas et al., "Construction of T-Vectors, A Rapid and General System for Direct Cloning of Unmodified PCR Products", *Nucleic Acids Research* 19(5):1154 (1991).

Martin, Joseph B. et al., "Huntington's Disease: Pathogenesis and Management", *The New England Journal of Medicine* 315(20):1267–1276 (Nov. 13, 1986).

Palczewski, Krzysztof et al., "G–Protein–Coupled Receptor Kinases", *TIBS* 16:387–391 (Oct. 1991).

Sibley, David R. et al., "Regulation of Transmembrane Signaling by Receptor Phosphorylations", *Cell* 48:913–922 (Mar. 27, 1987).

Smith, Barbara et al., "Isolation of DNA Markers in the Direction of the Huntington Disease Gene from the G8 Locus", *Am. J. Hum. Genet.* 42:335–344 (1988).

Snell, Russell G., "Linkage Disequilibrium in Huntington's Disease: An Improved Localisation for the Gene", *Journal of Medical Genetics* 26:673–675 (1989).

Snell, Russell G., "A Recombination Event That Redefines the Huntington Disease Region", *Am.J. Hum. Genet.* 51:357–362 (1992).

Taylor, S. A. M., "A Dinucleotide Repeat Polymorphism at the D4S127 Locus", *Human Molecular Genetics* 1(2):142 (1992).

Theilmann, J. et al., "Non–Random Association Between Alleles Detected At D4S95 and D3S98 and the Huntington's Disease Gene", *Journal of Medical Genetics* 26:676–681 (1989).

Verkerk, Annemieke J. M. H. et al., "Identification of a Gene (FMR–1) Containing a CGG Repeat Coincident with a Breakpoint Cluster Region Exhibiting Length Variation in Fragile X Syndrome", *Cell* 65:905–914 (May 31, 1991).

```
  1  GCAGCCGCCG CGGTCGGGCT GCCCCCTCCC CTCGCCCCGA CCGCTCCCCT

51  GCTGGTGAGG GCCTGCGCAG GCGGCGGCGG CGGCGCCCTT GGTGGCAGTG

101  GTGGCGGCGG AGCAGCCTCC CGGGATCGTG TCTGGAGCTC GAGGAGAGGG

151  TAGTGCCCGG CGAGCTATGC ACGGGGGCGG CGGCGTCTCC TCCTGTTCCG

201  CCTCCTCAGT CTCCTCGGTC TCGCAGAATC CGCCGGCGGC GGCGGCGCCA

251  GGACATGGAG CTCGAGAACA TCGTGGCCAA CTCGCTGCTG CTGAAAGCGC
             M  E   L  E  N  I   V  A  N   S  L  L    L  K  A  R

301  GTCAAGAAAA GGATTATAGC AGTCTTTGTG ACAAGCAACC GATAGGAAGA
      Q  E  K    D  Y  S   S  L  C  D   K  Q  P   I  G  R

351  CGTCTCTTCA GGCAGTTCTG TGATACCAAA CCCACTCTAA AGAGGCACAT
      R  L  F  R   Q  F  C   D  T  K   P  T  L  K    R  H  I

401  TGAATTCTTG GATGCAGTGG CAGAATATGA AGTTGCCGAT GATGAGGACC
       E  F  L   D  A  V  A   E  Y  E   V  A  D   D  E  D  R

451  GAAGTGATTG TGGACTGTCA ATCTTAGATA GATTCTTCAA TGATAAGTTG
       S  D  C   G  L  S   I  L  D  R   F  F  N   D  K  L

501  GCAGCCCCTT TACCAGAAAT ACCTCCAGAT GTTGTGACAG AATGTAGATT
      A  A  P  L   P  E  I   P  P  D   V  V  T  E    C  R  L

551  GGGACTGAAG GAGGAGAACC CTTCCAAAAA AGCCTTTGAG GAATGTACTA
      G  L  K   E  E  N  P    S  K  K   A  F  E   E  C  T  R

601  GAGTTGCCCA TAACTACCTA AGAGGGGAAC CATTTGAAGA ATACCAAGAA
       V  A  H   N  Y  L   R  G  E  P   F  E  E   Y  Q  E

651  AGCTCATATT TTTCTCAGTT TTTACAATGG AAATGGCTGG AAAGGCAACC
       S  S  Y  F   S  Q  F   L  Q  W   K  W  L   E  R  Q  P

701  CGTAACAAAG AACACATTTA GACATTACAG AGTTCTAGGA AAAGGCGGAT
       V  T  K   N  T  F  R    H  Y  R   V  L  G   K  G  G  F
```

FIG.2A

```
 751  TTGGAGAGGT TTGCGCCTGT CAAGTGCGAG CCACAGGAAA AATGTATGCC
        G  E  V   C  A  C   Q  V  R    T  G  K    M  Y  A

801  TGCAAAAAGC TACAAAAAAA AAGAATAAAG AAGAGGAAAG GTGAAGCTAT
        C  K  K   L  Q  K   K  R  I    K  K  R  K  G  E  A  H

851  GGCTCTAAAT GAGAAAAGAA TTCTGGAGAA AGTGCAAAGT AGATTCGTAG
        A  L  N   E  K  R   I  L  E  K    V  Q  S    R  F  V  V

901  TTAGTTTAGC CTACGCTTAT GAAACCAAAG ATGCCTTGTG CTTGGTGCTC
        S  L  A   Y  A  Y   E  T  K  D    A  L  C    L  V  L

951  ACCATTATGA ATGGAGGGGA TTTGAAGTTT CACATTTACA ACCTGGGCAA
        T  I  M  N   G  G  D    L  K  F    H  I  Y  N    L  G  N

1001  TCCCGGCTTT GATGAGCAGA GAGCCGTTTT CTATGCTGCA GAGCTGTGTT
        P  G  F   D  E  Q  R    A  V  F    Y  A  A    E  L  C  C

1051  GCGGCTTGGA AGATTTACAG AGGGAAAGAA TTGTATACAG AGACTTGAAG
        G  L  E   D  L  Q   R  E  R  I    V  Y  R    D  L  K

1101  CCTGAGAATA TTCTCCTTGA TGATCGTGGA CACATCCGGA TTTCAGACCT
        P  E  N  I    L  L  D   D  R  G    H  I  R  I    S  D  L

1151  CGGTTTGGCC ACAGAGATCC CAGAAGGACA GAGGGTTCGA GGAAGAGTTG
        G  L  A   T  E  I  P    E  G  Q    R  V  R    G  R  V  G

1201  GAACAGTCGG CTACATGGCA CCTGAAGTTG TCAATAATGA AAAGTATACG
        T  V  G   Y  M  A   P  E  V  V    N  N  E  K    Y  T

1251  TTTAGTCCCG ATTGGTGGGG ACTTGGCTGT CTGATCTATG AAATGATTCA
        F  S  P  D    W  W  G   L  G  C    L  I  Y  E    M  I  Q

1301  GGGACATTCT CCATTCAAAA AATACAAAGA GAAAGTCAAA TGGGAGGAGG
        G  H  S   P  F  K  K    Y  K  E    K  V  K    W  E  E  V

1351  TCGATCAAAG AATCAAGAAT GATACCGAGG AGTATTCTGA GAAGTTTTCA
        D  Q  R   I  K  N   D  T  E  E    Y  S  E  K    F  S
```

FIG.2B

```
1401  GAGGATGCCA AATCTATCTG CAGGATGTTA CTCACCAAGA ATCCAAGCAA
       E  D  A  K   S  I  C   R  M  L   L  T  K  N   P  S  K

1451  GCGGCTGGGC TGCAGGGGCG AGGGAGCGGC TGGGGTGAAG CAGCACCCCG
       R  L  G   C  R  G  E   G  A  A   G  V  K   Q  H  P  V

1501  TGTTCAAGGA CATCAACTTC AGGAGGCTGG AGGCAAACAT GCTGGAGCCC
       F  K  D   I  N  F   R  R  L  E   A  N  H   L  E  P

1551  CCTTTCTGTC CTGATCCTCA TGCCGTTTAC TGTAAGGACG TCCTGGATAT
       P  F  C  P   D  P  H   A  V  Y   C  K  D   V  L  D  I

1601  CGAGCAGTTC TCGGCGGTGA AAGGGATCTA CCTGGACACC GCAGATGAAG
       E  Q  F   S  A  V  K   G  I  Y   L  D  T   A  D  E  D
                  GTG
                  V

1651  ACTTCTATGC TCGGTTTGCT ACCGGGTGTG TCTCCATCCC CTGGCAGAAT
        F  Y  A   R  F  A   T  G  C  V   S  I  P   W  Q  N

1701  GAGGACTGCC TGACCATGGT CCCCAGTGAG AAGGAAGTGG AACCCAAGCA
       E  D  C  L   T  M  V   P  S  E   K  E  V   E  P  K  Q

1751  ATGCTGAGCA CCCCGGTGCG GACCACAGAG CAGACCCTGG CGCCAGGAAG
       C  *

1801  GAGCATGTGT TAGCGTCTCG TCCCACCTGG AATTGTAATA AATACATCTA

1851  AATAAAACAT GCCTTGGGAG TGTACAGACA AAAAAA
```

FIG.2C

DNA ENCODING A PROTEIN-COUPLED RECEPTOR KINASE

STATEMENT OF GOVERNMENT RIGHTS IN THE INVENTION

Part of the work performed during development of this invention utilized U.S. Government funds. The U.S. Government has certain rights in this invention.

BACKGROUND OF THE INVENTION

1. Field of the Invention

The present invention relates to the isolation of a DNA from locus 4p16 of chromosome 4, which encodes a novel member of a family of protein kinases that specifically phosphorylate the activated forms of G protein-coupled receptors, thereby desensitizing the receptor and blocking further signal transduction.

2. Background of the Invention

2.1 The G Protein-Coupled Receptor Kinases.

The G protein-coupled receptors mediate responses by guanine nucleotide-binding regulatory proteins (G-proteins) to a wide range of extracellular stimuli, including hormones, neurotransmitters, peptides, odorants, and light. Evidence has shown that G protein-coupled receptor desensitization may be caused by specific phosphorylation of the receptor. Palczewski and Benovic, TIBS 16:387-391 (1991). Furthermore, several investigators have proposed that phosphorylation of the receptor protein by highly specific receptor kinases may represent an important and unifying mechanism serving to dampen receptor function in the presence of persistent or excessive stimulation. Lorenz et al., Proc. Natl. Acad. Sci. U.S.A. 88:8715-8719 (1991). Biochemical data have demonstrated that the G protein-coupled receptor kinases are unique in their ability to recognize and phosphorylate only the stimulus-modified or activated conformations of the G protein-coupled receptors. Benovic et al., Proc. Natl. Acad. Sci. U.S.A. 83:2797-2801 (1986); Sibley et al., Cell 48:913-922 (1987); Benovic et al., Annu. Rev. Cell Biol. 4:405-428 (1988).

Two specific enzymes from the family of serine-/threonine kinases, which mediate stimulus-specific phosphorylation of G protein-coupled receptors have been characterized. Specifically, light activated rhodopsin has been shown to be phosphorylated and inactivated by rhodopsin kinase (ROK), whereas the agonist-occupied $\beta_2$-adrenergic receptor (and possibly other G protein-coupled receptors) has been shown to be phosphorylated and desensitized by the $\beta$-adrenergic receptor kinase ($\beta$ARK). Palczewski and Benovic, TIBS, supra (1991).

Currently, rhodopsin kinase has only been cloned from cattle (Lorenz et al, supra (1991)) and has yet to be mapped in mouse or man. However, two forms of $\beta$ARK have been identified to date, $\beta$ARK and $\beta$ARK2. $\beta$ARK has been cloned from cattle (Benovic et al., J. Biol. Chem. 269:9026-9032 (1987)), rat (Arriza et al., GENBANK accession number M87854) and man (Benovic et al., FEBS Lett. 283:122-126 (1991)), while $\beta$ARK2 has been cloned only from cattle (Benovic et al., J. Biol. Chem. 266:14939-14946 (1991)) and rat (Arriza et al., GENBANK accession number M878555). In addition, two new members of the family of G protein-coupled receptor kinases (GPRK), GPRK-1 and GPRK-2, have been recently cloned from Drosophila (Cassill et al., Proc. Natl. Acad. Sci. U.S.A. 88:11067-11070 (1991)). Although cloned from retina, the receptor kinases were ubiquitously expressed.

Both rhodopsin kinase and $\beta$ARK specifically phosphorylate the activated form of the corresponding receptor, increasing its ability to interact with retinal arrestin or $\beta$-arrestin, respectively. However, it is interesting to note that rhodopsin and $\beta$-adrenergic receptors can be properly phosphorylated by each other's kinase, albeit at lower affinity, and only in their active state. Cassill et al., supra (1991).

Phosphorylation alone has been shown to result in only a slight decrease in receptor activity, but causes the receptors to be high-affinity substrates for the arrestin proteins. The phosphorylation of the receptor by the kinase has been shown to be a prerequisite for arrestin binding; however, binding of the arrestins to the receptors then blocks further activation of the respective signal transduction pathways. In other words, the enzymatic chain of events effectively "turns off" the active state of the receptor by preventing the receptor from coupling to the G-protein. Gassill et al., supra (1991).

It is apparent from the foregoing that there is a long-felt need in the art to understand the biochemical mechanisms involved in receptor transduction pathways. Clearly, identification and characterization of a novel member of the family of protein kinases that specifically phosphorylate the activated forms of G protein-coupled receptors would significantly advance the art, particularly since the kinases are thought to desensitize the specific receptors, thereby blocking signal transduction. The present invention satisfies this need and provides related advantages in the art.

2.2 Identification of the Huntington's Disease Region.

Huntington's disease is an autosomal dominant progressive neurodegenerative disorder of mid-life onset involving uncontrolled choreic movements, psychiatric disturbance and cognitive decline. The disease is characterized by extensive neuronal cell death, particularly in the caudate nucleus. Martin and Gusella, New Engl. J. Med. 315:1267-1276 (1986).

To date, no biochemical mechanism underlying the expression of Huntington's disease has been explained in either patients afflicted with the disease, or in individuals genetically predisposed to the disorder. Bates et al., Am. J. Hunt. Genet. 49:7-16 (1991). However, it was recognized that molecular genetic methods could be utilized in an indirect approach, to search for a gene linked to Huntington's disease via chromosomal mapping, although no knowledge of the gene product was available. Previously, the more traditional route of searching for an aberrant protein was unlikely to be successful in Huntington's disease, given the complexity of the affected tissue, the strong likelihood of confounding secondary changes, and the lack of availability of brain tissue from patients afflicted with Huntington's disease until late in the course of the disorder. Gusella, Adv. Hum. Genet. 20:125-151 (1991).

As a result of the high penetrance of the Huntington's disease defect and of the relatively long course of the disease after the onset of symptoms, it has been possible to identify very large extended kindreds with many affected members. The strategy for identifying the region of the Huntington's disease defect within the human chromosome has involved using naturally occurring variations in DNA sequence in the human population as high-quality genetic markers for tracking the transmission of particular chromosomal regions through disease pedigrees. Gusella, *Adv. Hum. Genet., supra.*

The Huntington's disease region was first localized in 1983 by genetic linkage analysis using the DNA marker D4S10 and two Huntington's disease pedigrees, an extremely large Venezuelan family and a smaller 14 member American kindred. The disease gent was mapped to chromosome 4, marking the first instance in which a genetic defect had been mapped to a chromosome using only DNA marker linkage analysis. Gusella et al., *Nature* 306:234-238 (1983); Gusella et al., *Science* 225:1320-1326 (1984); see also U.S. Pat. No. 4,666,828, issued May 19, 1987.

As disclosed by Allitto et al. in *Genomics* 9:104-112 (1991), mapping of the DNA marker D4S10 by dosage studies in Wolf-Hirschhorn syndrome (Gusella et al., *Nature* 318:75-78, (1985)), by in situ hybridization (Zabel et al., *Cytogenet. Cell Genet.* 42:187-190 (1986); Magenis et al., *Amer. J. Hunt. Genet* 39:383-391 (1986); Wang et al., *Amer. J. Hum. Genet.* 39:392-396 (1986); Landegent et al., Hunt. Genet. 73:354-357 (1986)), and by somatic cell hybrid analysis (MacDonald et al., *Genomics* 1:29-34 (1987); Smith et al., *Amer. J. Hum. Genet.* 42:335-344 (1988)) has placed the marker in chromosomal locus 4p16. In addition, somatic cell hybrid panels were constructed to permit the mapping of DNA probes to either the proximal or the distal portions of 4p16.3. MacDonald et al., supra, (1987); Smith et al. supra, (1988).

The mapping of the Huntington's disease marker, D4S10, near the telomere of 4p has created the impetus for constructing detailed genetic and physical maps of the terminal segment of 4p. Allitto et al., supra. (1991). However, the critical issue in isolating the Huntington's disease gene has been to define which portion of the physical map contained the defect. In several other disorders, the identification of a disease gene has been facilitated by the observation of a physical rearrangement in the candidate region. Unfortunately, no such physical alteration has been reported for the region of the Huntington's disease defect. Gusella, *Adv. Hum. Genet., supra.*

Consequently, the only means available to establish the position of the defect on the physical map was to analyze Huntington's disease affected families in which recombination has occurred between the disease gene and markers of known position in 4p16.3. Gusella, *Adv. Hum. Genet., supra.* Attempts to isolate the Huntington's disease gene based on its position in the proximal portion of the terminal cytogenetic subband, 4p16.3, of chromosome 4, were frustrated by apparently contradictory recombination events.

However, more recent multipoint linkage mapping using a proximal marker has established that the Huntington's disease genetic region is located distal to D4S10 within 4p16.3, which constitutes 3% of the cytogenetic length of chromosome 4 or approximately 0.2 % of the total genome (Gilliam et al., *Cell* 50:565-571 (1987)). Moreover, using multi-allele polymorphisms to assess the consistency of the haplotypes present in the Huntington's disease region of the chromosome, MacDonald et al. have found that about one third of all Huntington's disease chromosomes derive from one primordial haplotype, which is most consistent in the proximal portion of the internal candidate region. See, *Nature Genet.* 1:99-103 (1992). Thus, haplotype analysis has indicated that a 500 kb segment between D4S180 and D4S182 was the most likely site of the genetic defect (MacDonald et al., supra (1992)).

It is apparent from the foregoing that there has remained a long-felt need in the art for the determination of the biochemical mechanism which results in Huntington's disease in genetically predisposed patients. Clearly, there has been great interest in the identification of a gene related to Huntington's disease, as well as a determination of its sequence and expression product to provide reliable probes for the detection of the disease in a patient. Such advances would permit a direct experimental approach to identifying the fundamental mechanisms involved in the activation of this devastating disease. Therefore, identification and characterization of a gene related to Huntington's disease would significantly advance the art.

BRIEF SUMMARY OF THE INVENTION

Recognizing the importance of identifying and characterizing genes within the Huntington's disease region of chromosome 4, the inventors have employed a powerful new method, exon amplification (Buckler et al., *Proc. Natl. Acad. Sci. U.S.A.* 88:4005-4009 (1991)) to isolate coding sequences from the region. The site between D4S180 and D4S182 that displayed the most striking linkage disequilibrium with Huntington's disease was a $(dGdT)_n$ polymorphism from cosmid BJ56, defining the D4S127 locus (MacDonald et al., supra (1992); Allitto et al., *Genomics* 9:104-112 (1991); Taylor et al., *Human Molecular Genetics* 1:142 (1992)). Consequently, the inventors have amplified and cloned several trapped exons from BJ56 and overlapping cosraids, and used these to isolate the corresponding cDNA, IT-11.

Sequence analysis revealed IT-11 to be a novel member of a family of mammalian G protein-coupled receptor kinases (Palczewski, K. and Benovic, J. L., TIBS 16:387-391 (1991)). The best-characterized members of this family, rhodopsin kinase (Lorenz et al., *Proc. Natl. Acad. Sci. U.S.A.* 88:8715-8719 (1991)), and β-adrenergic receptor kinases 1 and 2 (Benovic et al., *J. Biol. Chem.* 269:9026-9032 (1987); Benovic et al., *Science* 246:235-240 (1989)), are specific for the activated or ligand-bound form of the receptor and are thought to participate in receptor desensitization. Thus, discovery of this novel kinase and the gene encoding same adds to a growing family of mammalian G protein-coupled receptor kinases that play a crucial role in controlling signal transduction from a variety of receptors. It also provides the isolation of a novel expression product of a gene within the Huntington's disease region.

Accordingly, the invention is first directed to a DNA segment, IT-11, which maps within the terminal cytogenic subband of the short arm of chromosome 4,4p16.3, between DNA marker D4S10 and the telomere region.

The present invention further provides a DNA segment which encodes at least one member of the family of mammalian G protein-coupled receptor kinases. Further, this invention provides the substantially purified expression product having an amino acid sequence corresponding to IT-11, or its immunological equivalent.

The invention additionally includes diagnostic and therapeutic uses for the above described molecules.

This invention provides a nucleic acid probe for the detection of a DNA segment coding for IT-11. The invention also extends to products useful for carrying out a method of detection, such as DNA probes (labeled or unlabeled), kits and the like.

Accordingly, this invention provides a nucleic acid probe for the detection of a DNA segment coding for a mammalian G protein-coupled receptor kinase. Further, invention provides a method of detecting a mammalian G protein-coupled receptor kinase based on the detection of a DNA segment coding for a G protein-coupled receptor kinase. And, the invention also provides a method of detecting a DNA segment within the Huntington's disease region of chromosome 4.

Further, this invention provides a probe for the detection of the expression product of a DNA segment coding for a mammalian G protein-coupled receptor kinase. It also provides a probe for the detection of the expression product of a DNA segment within the Huntington's disease region.

Accordingly, this invention provides a method of detecting a mammalian G protein-coupled receptor kinase based on the detection of an expression product of a DNA segment coding for a mammalian G protein-coupled receptor kinase. And further, provided that IT-11 kinase contains the mutation related to Huntington's disease, this invention provides a method of detecting Huntington's disease based on the detection of an expression product of a gene within the Huntington's disease region, or its immunological equivalents.

In addition, the invention provides an assay and method of detection of the expression product of a gene from the Huntington's disease region of chromosome 4, which can be used prenatally to screen a fetus, or presymptomatically to screen a subject who is genetically predisposed to Huntington's disease based on his family history. Accordingly, this invention provides a diagnostic kit for the detection of the expression of IT-11, or its immunological equivalents.

The present invention provides antibodies which are capable of binding to an expression product of a DNA segment coding for a mammalian G protein-coupled receptor kinase, or its immunological equivalents. And, the present invention provides antibodies which are capable of binding to an expression product of a gene from the Huntington's disease region of chromosome 4, or its immunological equivalents.

The invention also provides a method of obtaining a recombinant or synthetic DNA molecule capable of encoding, or expressing IT-11, fragment thereof, or functional derivative thereof. Also, it provides a method of obtaining a recombinant or synthetic DNA molecule capable of encoding, or expressing a DNA segment coding for a mammalian G protein-coupled receptor kinase, or a functional derivative thereof.

Additional objects, advantages and novel features of the invention will be set forth in part in the description which follows, and in part will become apparent to those skilled in the an on examination of the following, or may be learned by practice of the invention.

Figure 1:
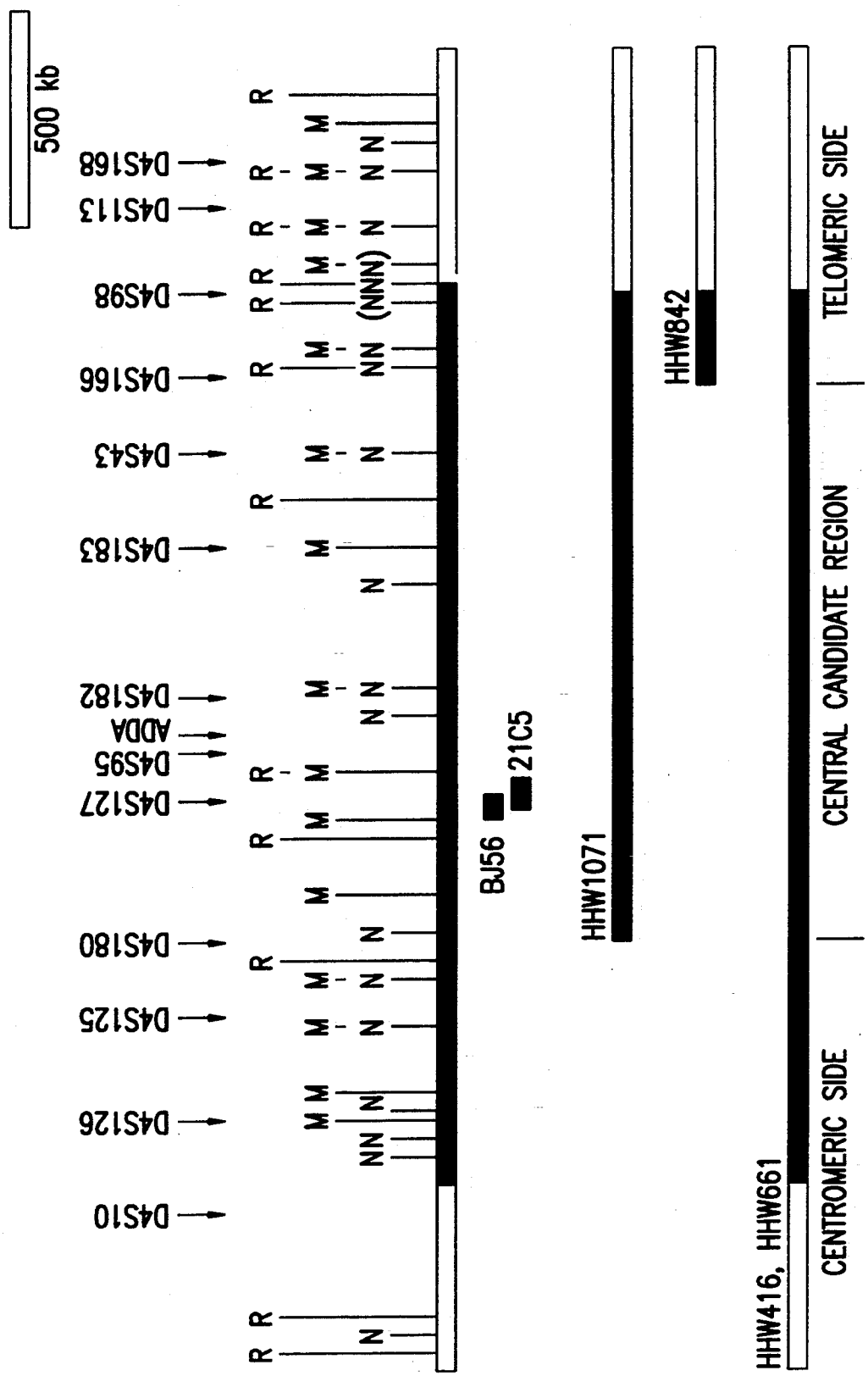
FIG. 1—Long-Range Restriction Map of the Huntington's Disease Region.

A partial long range restriction map of 4p16.3 is shown in which the Huntington's disease region is depicted as a filled line. Locus names above the map denote selected polymorphic markers that have been used to designate Huntington's disease families. Below the map, the regions of 4p16.3 present in somatic cell hybrids HHW1071, HHW842, HHW416 and HHW661 are illustrated. The position of D4S127 within the central portion is shown immediately below the map. Restriction sites are shown for Not I ("N"), Mlu I ("M") and Nru I ("R"). Sites displaying complete digestion are shown in boldface, while sites subject to frequent incomplete digestion are shown as lighter symbols. Brackets around the "N" symbols between D4S114 and D4S186 indicate the presence of additional clustered Not I sites.

FIG. 2A to 2C—Sequence of IT-11.

The 1886 base composite DNA sequence was derived from IT11-A, -B and -C. IT11-A spanned bases 156–1886. The 5' extension was derived from the overlapping clones IT11-B and -C which spanned bases 1-306 and 34-306, respectively. Two potential poly(A) addition sites, AATAAA, are underlined, as are sequences corresponding to the trapped exons, dBJ56-3 and d21C5. The alternative codon 454 created by sequence polymorphism is shown below the corresponding location in the sequence. The predicted amino acid sequence of 500 residues is shown below the DNA sequence, with the stop codon denoted by "*".

DEFINITIONS

In the description that follows, a number of terms used in recombinant DNA (rDNA) technology are extensively utilized. In order to provide a clear and consistent understanding of the specification and claims, including the scope to be given such terms, the following definitions are provided.

DNA Segment. A DNA segment, as is generally understood and used herein, refers to a molecule comprising a linear stretch of nucleotides wherein the nucleotides are present in a sequence that encodes, through the genetic code, a molecule comprising a linear sequence of amino acid residues that is referred to as a protein, a protein fragment or a polypeptide.

Gene. A DNA sequence related to a single polypeptide chain or protein, and as used herein includes the 5' and 3' ends. The polypeptide can be encoded by a full-length sequence or any portion of the coding sequence, so long as the functional activity of the protein is retained.

A "complementary DNA" or "cDNA" gene includes recombinant genes synthesized by reverse transcription of messenger RNA ("mRNA") lacking intervening sequences (introns).

Structural Gene. A DNA sequence that is transcribed into mRNA that is then translated into a sequence of amino acids characteristic of a specific polypeptide. Typically the first nucleotide of the first translated codon is numbered +1, and the nucleotides are numbered consecutively with positive integers through the translated region of the structural gene and into the 3' untranslated region. The numbering of the nucleotides in the promoter and regulatory region 5' to the translated region proceeds consecutively with negative integers with the 5' nucleotide next to the first translated nucleotide being numbered −1.

Huntington's Disease Genetic Region. The Huntington's disease genetic region (also Huntington's disease region) is located distal to D4S10 within 4p16.3 of chromosome 4. In particular, the Huntington's disease region is located between D4S 180 and D4S 182 within 4p16.3.

Restriction Endonuclease. A restriction endonuclease (also restriction enzyme) is an enzyme that has the capacity to recognize a specific base sequence (usually 4, 5, or 6 base pairs in length) in a double-stranded DNA molecule, and to cleave both strands of the DNA molecule at every place where this sequence appears. For example, EcoRI recognizes the base sequence GAATTC/CITAAG.

Restriction Fragment. The DNA molecules produced by digestion with a restriction endonuclease are referred to as restriction fragments. Any given genome will be digested by a particular restriction endonuclease into a discrete set of restriction fragments.

Agarose Gel Electrophoresis. To detect a polymorphism in the length of restriction fragments, an analytical method for fractionating double-stranded DNA molecules on the basis of size is required. The most commonly used technique (though not the only one) for achieving such a fractionation is agarose gel electrophoresis. The principle of this method is that DNA molecules migrate through the gel as though it were a sieve that retards the movement of the largest molecules to the greatest extent and the movement of the smallest molecules to the least extent. Note that the smaller the DNA fragment, the greater the mobility under electrophoresis in the agarose gel.

The DNA fragments fractionated by agarose gel electrophoresis can be visualized directly by a staining procedure if the number of fragments included in the pattern is small. The DNA fragments of genomes can be visualized successfully. However, most genomes, including the human genome, contain far too many DNA sequences to produce a simple pattern of restriction fragments. For example, the human genome is digested into approximately 1,000,000 different DNA fragments by EcoRI. In order to visualize a small subset of these fragments, a methodology referred to as the Southern hybridization procedure can be applied.

Southern Transfer Procedure. The purpose of the Southern transfer procedure (also referred to as blotting) is to physically transfer DNA fractionated by agarose gel electrophoresis onto a nitrocellulose filter paper or another appropriate surface or method, while retaining the relative positions of DNA fragments resulting from the fractionation procedure. The methodology used to accomplish the transfer from agarose gel to nitrocellulose involves drawing the DNA from the gel into the nitrocellulose paper by capillary action.

Nucleic Acid Hybridization. Nucleic acid hybridization depends on the principle that two single-stranded nucleic acid molecules that have complementary base sequences will reform the thermodynamically favored double-stranded structure if they are mixed in solution under the proper conditions. The double-stranded structure will be formed between two complementary single-stranded nucleic acids even if one is immobilized on a nitrocellulose filter. In the Southern hybridization procedure, the latter situation occurs. As noted previously, the DNA of the individual to be tested is digested with a restriction endonuclease, fractionated by agarose gel electrophoresis, converted to the single-stranded form, and transferred to nitrocellulose paper, making it available for reannealing to the hybridization probe.

Hybridization Probe. To visualize a particular DNA sequence in the Southern hybridization procedure, a labeled DNA molecule or hybridization probe is reacted to the fractionated DNA bound to the nitrocellulose filter. The areas on the filter that carry DNA sequences complementary to the labeled DNA probe become labeled themselves as a consequence of the reannealing reaction. The areas of the filter that exhibit such labeling are visualized. The hybridization probe is generally produced by molecular cloning of a specific DNA sequence from the human genome.

Oligonucleotide or Oligomer. A molecule comprised of two or more deoxyribonucleotides or ribonucleotides, preferably more than three. Its exact size will depend on many factors, which in turn depend on the ultimate function or use of the oligonucleotide. An oligonucleotide may be derived synthetically or by cloning.

Sequence Amplification. A method for generating large amounts of a target sequence. In general, one or more amplification primers are annealed to a nucleic acid sequence. Using appropriate enzymes, sequences found adjacent to, or in between the primers is amplified.

Amplification Primer. An oligonucleotide which is capable of annealing adjacent to a target sequence and serving as an initiation point for DNA synthesis when placed under conditions in which synthesis of a primer extension product which is complementary to a nucleic acid strand is initiated.

Cloning Vector. A plasmid or phage DNA or other DNA sequence which is used to "carry" inserted foreign DNA for the purpose of producing more material or protein product. The vector may replicate autonomously in a host cell, and may be characterized by one or a small number of endonuclease recognition sites at which such DNA sequences may be cut in a determinable fashion without loss of an essential biological function of the vehicle, and into which DNA may be spliced in order to bring about its replication and cloning. The cloning vector may further contain a marker suitable for use in the identification of cells transformed with the cloning vector. Markers, for example, are tetracycline resistance or ampicillin resistance. The word "cloning vehicle" may be used for "vector" or "cloning vector."

Expression. Expression is the process by which a structural gene produces a polypeptide. It involves transcription of the gene into mRNA, and the translation of such mRNA into polypeptide(s).

Expression Vector. A cloning vector or vehicle designed so that a cloned gene or coding sequence inserted at a particular site will be transcribed and translated into protein. The cloned gene is may be placed under the control of (i.e., "operably linked to") certain control sequences, such as promoter sequences.

Expression control sequences will vary depending on whether the vector is designed to express the operably linked gene in a prokaryotic or eukaryotic host and may additionally contain transcriptional elements, such as enhancer elements, termination sequences, tissue-specificity elements, and/or translational initiation and termination sites.

The present invention pertains both to expression of a G protein-coupled receptor kinase gene, and to the functional derivatives of the expression product.

Functional Derivative. A "functional derivative" of G protein-coupled receptor a kinase sequence, either protein or nucleic acid, is a molecule that possesses a biological activity (either functional or structural) that is substantially similar to a biological activity of a non-recombinant G protein-coupled receptor kinase protein or nucleic acid. A functional derivative of a G protein-coupled receptor kinase protein may or may not contain post-translational modifications such as covalently linked carbohydrate, depending on the necessity of such modifications for the performance of a specific function. The term "functional derivative" is intended to include the "fragments," "segments," "variants," "analogs," or "chemical derivatives" of a molecule.

As used herein, a molecule is said to be a "chemical derivative" of another molecule when it contains additional chemical moieties not normally a part of the molecule. Such moieties may improve the molecule's solubility, absorption, biological half life, and the like. The moieties may alternatively decrease the toxicity of the molecule, eliminate or attenuate any undesirable side effect of the molecule, and the like. Moieties capable of mediating such effects are disclosed in *Remington's Pharmaceutical Sciences* (1980). Procedures for coupling such moieties to a molecule are well known in the art.

Fragment. A "fragment" of a molecule such as a G protein-coupled receptor kinase protein or nucleic acid is meant to refer to any portion or a native G protein-coupled receptor kinase amino acid or nucleotide genetic sequence.

Variant. A "variant" of a G protein-coupled receptor kinase protein or nucleic acid is meant to refer to a molecule substantially similar in structure and biological activity to either a native G protein-coupled receptor kinase molecule, or to a fragment thereof. Thus, provided that two molecules possess a common activity and may substitute for each other, they are considered variants as that term is used herein even if the composition or secondary, tertiary, or quaternary structure of one of the molecules is not identical to that found in the other, or if the amino acid or nucleotide sequence is not identical.

Analog. An "analog" of a G protein-coupled receptor kinase protein or genetic sequence is meant to refer to a protein or genetic sequence substantially similar in function to a G protein-coupled receptor kinase protein or genetic sequence described herein. For example, analogs of a G protein-coupled receptor kinase protein described herein include G protein-coupled receptor kinase isozymes and analogs of the G protein-coupled receptor kinase genetic sequences described herein include G protein-coupled receptor kinase alleles.

Allele. An alternative form of a gene. In most organisms there are two alleles of any one gene (one from each parent) which occupy the same relative position on homologous chromosomes. Homozygous organisms have two identical alleles controlling a particular feature (these may be either dominant or recessive). Heterozygous organisms have two different alleles controlling a particular feature. The aspect of the feature displayed by the organism will be that determined by the dominant allele.

Substantially Pure. A "substantially pure" G protein-coupled receptor kinase protein is an G protein-coupled receptor kinase protein preparation that is generally lacking in other cellular components, and especially other non-Huntington's disease-linked proteins. "Substantially pure" G protein-coupled receptor kinase DNA is an G protein-coupled receptor kinase DNA preparation that is generally lacking in other cellular components, and especially in other non-G protein-coupled receptor kinase DNA.

DESCRIPTION OF THE PREFERRED EMBODIMENTS

The present invention relates to a novel DNA sequence, which has been identified as a novel member of a family of mammalian G protein-coupled receptor kinases. Furthermore, based on its location in human chromosome 4, the DNA sequence provides a novel expression product of a gene from the Huntington's disease region of chromosome 4.

A. DNA Segment.

At its broadest, the invention comprises a previously undisclosed DNA segment encoding a novel G protein-coupled receptor kinase which maps to the Huntington disease region of the human chromosome. In particular, the isolated DNA segment is IT-11, which encodes the expression product IT-11 peptide.

A.1. Isolation of DNA.

In one aspect of the present invention, a DNA segment coding for a polypeptide having an amino acid sequence corresponding to IT-11 is provided. In particular, the DNA segment may be isolated from a biological sample; more particularly from a biological sample containing nucleated cells. Most particularly the nucleated cells are obtained from a human.

One skilled in the art will realize that the human genome may be subject to slight allelic variations between individuals. Therefore, the isolated DNA segment is also intended to include allelic variations, so long as the sequence is a functional derivative of the G protein-coupled receptor kinase gene.

Furthermore, the biological sample may be obtained from a normal individual, or from one with a genetic predisposition for Huntington's disease, or from a patient afflicted with symptomatic Huntington's disease. As used herein, the term "normal" means those individuals that do not display a genetic predisposition for Huntington's disease, or any Huntington's disease as measured by clinical, symptomatic or morphological means. As used herein, the term "individuals with a genetic predisposition for Huntington's disease" is meant to include individuals, in particular humans, that may not yet show or display any Huntington's disease symptoms, as measured by symptomatic means, but may be inclined to develop Huntington's disease based on the genetic character of the individual's parents and grandparents.

Suitable biological samples having nucleated cells that may be used in this invention include, but are not limited to, blood, semen and tissue. The method of obtaining the biological sample will vary depending upon the nature of the sample.

By the term "nucleated cells" is meant any cell containing a nucleus. Examples of such cells include, but are not limited to, white blood cells, epithelial cells, sperm cells, or mesenchymal cells. Such cells may either be normal or neoplastic.

The nucleated cells are isolated from the sample and the DNA from the nucleated cells may be purified using means known in the art. For instance, DNA can be isolated by chemical synthesis or by isolation from an appropriate chromosomal library or cDNA library. DNA may also be isolated using size exclusion chromatography. In particular, the DNA segment may be determined by exon amplification.

A genetic sequence is suitable for expression in a host if it is uninterrupted by introns. The sequence is preferably in an excisable and recoverable form suitable for cloning into an appropriate vector.

A.2. Synthesis of DNA.

In the alternative, the DNA segment of the present invention may be chemically synthesized. For example, a DNA fragment with the nucleotide sequence which codes for the expression product of a gene from the Huntington's disease region of the chromosome may be designed and, if necessary, divided into appropriate smaller fragments. Then an oligomer which corresponds to the DNA fragment, or to each of the divided fragments, may be synthesized. Such synthetic oligonucleotides may be prepared, for example, by the triester method of Matteucci et al., *J. Am. Chem. Soc.* 103:3185–3191 (1981) or by using an automated DNA synthesizer.

An oligonucleotide may be derived synthetically or by cloning. If necessary, the 5'-ends of the oligomers may be phosphorylated using T4 polynucleotide kinase. Kinasing of single strands prior to annealing or for labeling may be achieved using an excess of the enzyme. If kinasing is for the labeling of probe, the ATP may contain high specific activity radioisotopes. Then, the DNA oligomer may be subjected to annealing and ligation with T4 ligase or the like.

A.3. DNA as a Probe or Printer.

In another embodiment of this invention, a DNA fragment may be used to probe an appropriate chromosomal or cDNA library by usual hybridization methods to obtain the segment of the present invention. The preferred method of hybridization is exemplified by Gusella et al. in *Nature* 306:234–238 (1983). In particular, it is most preferred to use nylon filters containing the phage DNA. In the alternative, chemical synthesis is carried out in order to obtain DNA fragments having nucleotide sequences which correspond to N-terminal and C-terminal portions of the amino acid sequence of the polypeptide of interest. Thus, the synthesized DNA fragments may be used as primers in a polymerase chain reaction (PCR) carried out in accordance with recognized PCR techniques, essentially according to *PCR Protocols, A Guide to Methods and Applications*, edited by Michael et al., Academic Press, 1990, utilizing the appropriate chromosomal or cDNA library to obtain the fragment of the present invention.

A chromosomal DNA or cDNA library, such as the library relied upon in the Examples of the present invention, may be prepared from appropriate cells according to recognized methods in the art (cf. *Molecular Clotting: A Laboratory Manual, second edition*, edited by Sambrook, Fritsch, & Maniatis, Cold Spring Harbor Laboratory, 1989).

B. Methods for Detecting the Presence of the DNA.

In a preferred embodiment of the present invention, methods are provided for detecting the presence of a DNA segment from the Huntington's disease region of chromosome 4. In particular, the method involves analyzing DNA using a hybridization probe which will hybridize to sequences encoding, or complimentary to a gene from the Huntington's disease region. In another embodiment, the method involves analyzing human DNA using a hybridization probe which will hybridize to sequences encoding, or complimentary to a G protein-coupled receptor kinase. Most particularly, the method involves analyzing DNA using a hybridization probe which will hybridize to sequences encoding, or complementary to IT-11.

In a further preferred embodiment of the invention, the probe utilized in the present method can be based on the DNA sequence of a gene from the Huntington's disease region of chromosome 4. More specifically, the probe utilized in the present method can be based on the DNA sequence of a mammalian G protein-coupled receptor kinase gene. In particular, the probe utilized in the present method can be based on the DNA sequence of a mammalian G protein-coupled receptor kinase gene comprising the nucleotide sequence IT-11. Moreover, a probe may be based on an allele of the gene.

One skilled in the art can readily design such probes based on the sequence disclosed herein using methods of computer alignment and sequence analysis known in the art.

The hybridization probes of the present invention can be labeled by standard labeling techniques such as with a radiolabel, enzyme label, fluorescent label, biotin-avidin label, chemiluminescence, and the like. After hybridization, the probes may be visualized using known methods.

A genetic predisposition for Huntington's disease, if present, may be detectable using the herein described hybridization probe to hybridize to a specific gene from the Huntington's disease region. Comparison studies with known standards may reveal the presence or absence of a specific gene from the Huntington's disease region.

The isolated DNA may be characterized by digestion(s) with a restriction enzyme. Such enzymes include, but are not limited to, HindIII, PstI, or EcoRI and the like. The DNA fragments are then separated according to their molecular weights to form a pattern or map, typically using electrophoresis. Alternately the isolated DNA may be characterized by recognized sequencing techniques, or more particularly, by commercially available methods and preparations.

Also included within the scope of this invention are the functional equivalents of the herein-described DNA or nucleotide sequences. The degeneracy of the genetic code permits substitution of certain codons by other codons which specify the same amino acid and hence would give rise to the same protein. The DNA or nucleotide sequence can vary substantially since, with the exception of methionine and tryptophan, the known amino acids can be coded for by more than one codon. Thus, portions or all of the disclosed IT-11 gene from the Huntington's disease region could be synthesized to give a DNA sequence significantly different from that shown in FIG. 2. The encoded amino acid sequence thereof would, however, be preserved.

In addition, the DNA or nucleotide sequence may comprise a nucleotide sequence which results from the addition, deletion or substitution of at least one nucleotide to the 5'-end and/or the 3'-end of the DNA formula of FIG. 2, or a derivative thereof. Any nucleotide or polynucleotide may be used in this regard, provided that its addition, deletion or substitution does not alter the amino acid sequence of FIG. 2 which is encoded by the nucleotide sequence. For example, the present invention is intended to include any nucleotide sequence resulting from the addition of ATG as an initiation codon at the 5'-end of the inventive nucleotide sequence or its derivative, or from the addition of TTA, TAG or TGA as a termination codon at the 3'-end of the inventive nucleotide sequence or its derivative. Moreover, the DNA fragment of the present invention may, as necessary, have restriction endonuclease recognition sites added to its 5'-end and/or 3'-end.

Such functional alterations of a given DNA or nucleotide sequence afford an opportunity to promote secretion and/or processing of heterologous proteins encoded for by foreign DNA sequences fused thereto. All variations of the nucleotide sequence of the disclosed IT-11 gene from the Huntington's disease region and fragments thereof permitted by the genetic code are, therefore, included in this invention.

Further, it is possible to delete codons or to substitute one or more codons by codons other than degenerate codons to produce a structurally modified polypeptide, but one which has substantially the same utility or activity of the polypeptide produced by the unmodified DNA molecule. As recognized in the art, the two polypeptides are functionally equivalent, as are the two DNA molecules which give rise to their production, even though the differences between the DNA molecules are not related to degeneracy of the genetic code.

The nucleic acid probes of the present invention include RNA, as well as DNA probes, such probes being generated using techniques known in the art.

In one embodiment of the above described method, a nucleic acid probe is immobilized on a solid support. Examples of such solid supports include, but are not limited to, plastics such as polycarbonate, complex carbohydrates, such as agarose or sepharose, and acrylic resins, such as polyacrylamide or latex beads. Techniques for coupling nucleic acid probes to such solid supports are well known in the art.

C. Peptide.

The present invention is further based on the observation that the DNA segment described herein as encoding the novel G protein-coupled receptor kinase which maps in the Huntington's disease region, in particular IT-11, contains an open reading frame which is capable of being translated into a unique peptide. In particular, the coding region is capable of being translated into a peptide whose amino acid sequence is depicted in SEQ ID:NO.2 (hereinafter the IT-11 peptide). Thus, the present invention is further directed to the peptide, in particular IT-11, substantially free of natural contaminants.

Utilizing this observation, 1) antibodies are described which are capable of binding to this peptide, 2) methods for detecting a predisposition for and the appearance of Huntington's disease based on identifying the peptide are described, and 3) methods are described for selectively inhibiting the expression of this peptide based on anti-sense gene expression technology.

A variety of methodologies known in the art can be utilized to obtain the peptide of the present invention. In one embodiment, the peptide is purified from tissues or cells which naturally produce the peptide. The samples of the present invention include cells, protein extracts or membrane extracts of cells, or biological fluids. The sample will vary based on the assay format, the detection method and the nature of the tissues, cells or extracts used as the sample.

Any eukaryotic organism can be used as a source for the peptide, as long as the source organism naturally contains such a peptide, in particular IT-11. As used herein, "source organism" refers to the original organism from which the amino acid sequence of the subunit is derived, regardless of the organism the subunit is expressed in and ultimately isolated from. For example, the IT-11 peptide expressed in hamster cells is of human origin as long as the amino acid sequence is that of SEQ ID:NO.2. The most preferred source organism is human.

One type of test sample which can be utilized in the present invention is derived from amniotic fluid or cells. Such a test sample is utilized to identify fetuses which carry a human gene for Huntington's disease.

D. Methods of Providing the Peptide.

D.1. Isolation of the Peptide and Its Functional Derivatives.

One skilled in the art can readily follow known methods for isolating proteins in order to obtain the peptide free of natural contaminants. These include, but are not limited to: immunochromotography, size-exclusion chromatography, HPLC, ion-exchange chromatography, and immuno-affinity chromatography.

There are a variety sources encoding a peptide. The peptide can be isolated as described herein from any source having the peptide, preferably having the IT-11 peptide. Preferably, the peptide can be isolated from a mammalian source; most preferably, from a human source. In the alternative, the sequence encoding a peptide, preferably an IT-11 peptide, can be synthesized by methods known in the art or expressed by methods disclosed herein.

D.2. Expression of the Peptide and Its Functional Derivatives.

In another embodiment, a peptide, preferably an IT-11 peptide, is purified from cells which have been altered to express the peptide.

As used herein, a cell is said to be "altered to express a desired peptide" when the cell, through genetic manipulation, is made to produce a protein which it normally does not produce or which the cell normally produces at low levels. One skilled in the art can readily adapt procedures for introducing and expressing either genomic, cDNA, or synthetic sequences into either eukaryotic or prokaryotic cells in order to generate a cell which produces the peptide, in particular the IT-11 peptide.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding a gene from the Huntington's disease region may be obtained by the above-described methods. This region may be retained for its transcriptional termination regulatory sequences, such as termination and polyadenylation. Thus, by retaining the 3'-region naturally contiguous to the DNA sequence encoding the gene, the transcriptional termination signals may be provided. Where the transcriptional termination signals are not satisfactorily functional in the expression host cell, then a 3' region functional in the host cell may be substituted.

Two DNA sequences (such as a promoter region sequence and an IT-11 sequence) are said to be operably linked if the nature of the linkage between the two DNA sequences does not (1) result in the introduction of a frame-shift mutation, (2) interfere with the ability of the promoter region sequence to direct the transcription of the gene sequence, or (3) interfere with the ability of the gene sequence to be transcribed by the promoter region sequence. Thus, a promoter region would be operably linked to a DNA sequence if the promoter were capable of effecting transcription of that DNA sequence.

Thus, to express a gene from the Huntington's disease region, transcriptional and translational signals recognized by an appropriate host are necessary.

The present invention encompasses the expression of the IT-11 protein (or a functional derivative thereof) in either prokaryotic or eukaryotic cells. Prokaryotic hosts are, generally, the most efficient and convenient for the production of recombinant proteins and, therefore, are preferred for the expression of the IT-11 gene.

Prokaryotes most frequently are represented by various strains of *E. coli*. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC18, pUC19 and the like; suitable phage or bacteriophage vectors may include λgt10, λgt11 and the like; and suitable virus vectors may include pMAM-neo, pKRC and the like. Preferably, the selected vector of the present invention has the capacity to replicate in the selected host cell.

Recognized prokaryotic hosts include bacteria such as *E. coli*, Bacillus, Streptomyces, Pseudomonas, Salmonella, Serratia, and the like. However, under such conditions, the peptide will not be glycosylated. The prokaryotic host must be compatible with the replicon and control sequences in the expression plasmid.

To express IT-11 (or a functional derivative thereof) in a prokaryotic cell, it is necessary to operably link the coding sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage λ ($P_L$ and $P_R$), the trp, recA, lacZ, lacI, and gal promoters of *E. coli*, the α-amylase (Ulmanen et al., *J. Bacteriol.* 162: 176–182 (1985)) and the ξ-28-specific promoters of *B. subtilis* (Gilman et al., *Gene sequence* 32:11–20 (1984)), the promoters of the bacteriophages of Bacillus (Gryczan, In: *The Molecular Biology of the Bacilli*, Academic Press, Inc., N.Y. (1982)), and Streptomyces promoters (Ward et al., *Mol. Gen. Genet.* 203:468–478 (1986)).

Prokaryotic promoters are reviewed by Glick (*J. Ind. Microbiol.* 1:277–282 (1987)); Cenatiempo (*Biochimie* 68:505–516 (1986)); and Gottesman (*Ann. Rev. Genet.* 18:415–442 (1984)).

Proper expression in a prokaryotic cell also requires the presence of a ribosome binding site upstream of the gene sequence-encoding sequence. Such ribosome binding sites are disclosed, for example, by Gold et al. (*Ann. Rev. Microbiol.* 35:365–404 (1981)).

The selection of control sequences, expression vectors, transformation methods, and the like, are dependent on the type of host cell used to express the gene. As used herein, "cell", "cell line", and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the peptide, preferably the IT-11 peptide. Suitable hosts may often include eukaryotic cells.

Preferred eukaryotic hosts include, for example, yeast, fungi, insect cells, mammalian cells either in vivo, or in tissue culture. Mammalian cells which may be useful as hosts include HeLa cells, cells of fibroblast origin such as VERO or CHO-K1, or cells of lymphoid origin, such as the hybridoma SP2/O-AG14 or the myeloma P3x63Sg8, and their derivatives. Preferred mammalian host cells include SP2/0 and J558L, as well as neuroblastoma cell lines such as IMR 332 that may provide better capacities for correct post-translational processing.

In addition, plant cells are also available as hosts, and control sequences compatible with plant cells are available, such as the nopaline synthase promoter and polyadenylation signal sequences.

Another preferred host is an insect cell, for example the Drosophila larvae. Using insect cells as hosts, the Drosophila alcohol dehydrogenase promoter can be used. Rubin, *Science* 240:1453–1459 (1988). Alternatively, baculovirus vectors can be engineered to express large amounts of IT-11 in insects cells (Jasny, *Science* 238:1653 (1987); Miller et al., In: *Genetic Engineering* (1986), Setlow, J. K., et al., eds., Plenum, Vol. 8, pp. 277–297).

Any of a series of yeast gene sequence expression systems can be utilized which incorporate promoter and termination elements from the actively expressed gene sequences coding or glycolytic enzymes are produced in large quantities when yeast are grown in mediums rich in glucose. Known glycolytic gene sequences can also provide very efficient transcriptional control signals.

Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). For a mammalian host, several possible vector systems are available for the expression of the peptide, preferably IT-11.

A wide variety of transcriptional and translational regulatory sequences may be employed, depending upon the nature of the host. The transcriptional and translational regulatory signals may be derived from viral sources, such as adenovirus, bovine papilloma virus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

As discussed above, expression of a kinase in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273–288 (1982)); the TK promoter of Herpes virus (McKnight, *Cell* 31:355–365 (1982)); the SV40 early promoter (Benoist et al., *Nature* (London) 290:304–310 (1981)); the yeast gal4 gene sequence promoter (Johnston et al., *Proc. Natl. Acad. Sci.* (U.S.A.) 79:6971–6975 (1982); Silver et al., *Proc. Natl. Acad. Sci.* (U.S.A.) 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes the kinase (or a functional derivative thereof) does not contain any intervening codons which are capable of encoding a methionine (i.e., AUG). The presence of such codons results either in a formation of a fusion protein (if the AUG codon is in the same reading frame as, for example, an IT-11 coding sequence) or a frame-shift mutation (if the AUG codon is not in the same reading frame as, for example, an IT-11 coding sequence).

A genetic coding sequence, e.g., IT-11, and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the gene may occur through the transient expression of the introduced sequence. Alternatively, permanent expression may occur through the integration of the introduced DNA sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, *Molec. Cell. Biol.* 3:280 (1983).

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, $\pi$VX. Such plasmids are, for example, disclosed by Maniatis et al. (In: *Molecular Cloning, A Laboratory Manual*, Cold Spring Harbor Press, Cold Spring Harbor, N.Y. (1982)). Bacillus plasmids include pC194, pC221, pT127, and the like. Such plasmids are disclosed by Gryczan (In: *The Molecular Biology of the Bacilli*, Academic Press, N.Y. (1982), pp. 307–329). Suitable Streptomyces plasmids include pIJ101 (Kendall et al., *J. Bacteriol.* 169:4177–4183 (1987)), and streptomyces bacteriophages such as $\phi$C31 (Chater et al., In: *Sixth International Symposium on Actinomycetales Biology*, Akademiai Kaido, Budapest, Hungary (1986), pp. 45–54). Pseudomonas plasmids are reviewed by John et al. (*Rev. Infect. Dis.* 8:693–704 (1986)), and Izaki (*Jpn. J. Bacteriol.* 33:729–742 (1978)).

Preferred eukaryotic plasmids include, for example, BPV, vaccinia, SV40, 2-micron circle, and the like, or their derivatives. Such plasmids are well known in the art (Botstein et al., *Miami Wntr. Symp.* 19:265–274 (1982); Broach, In: *The Molecular Biology of the Yeast Saccharomyces:* Life Cycle and Inheritance, Cold Spring Harbor Laboratory, Cold Spring Harbor, N.Y., p. 445–470 (1981); Broach, *Cell* 28:203–204 (1982); Bollon et al., *J. Clin. Hematol. Oncol.* 10:39–48 (1980); Maniatis, In: *Cell Biology: A Comprehensive Treatise*, Vol. 3, Gene Sequence Expression, Academic Press, N.Y., pp. 563–608 (1980)).

Once the vector or DNA sequence containing the construct(s) has been prepared for expression, the DNA construct(s) may be introduced into an appropriate host cell by any of a variety of suitable means, i.e., transformation, transfection, conjugation, protoplast fusion, electroporation, calcium phosphate-precipitation, direct microinjection, and the like. After the introduction of the vector, recipient cells are grown in a selective medium, which selects for the growth of vector-containing cells. Expression of the cloned gene sequence(s) results in the production of the peptide, in particular IT-11, or fragments thereof. This can take place in the transformed cells as such, or following the induction of these cells to differentiate (for example, by administration of bromodeoxyuracil to neuroblastoma cells or the like).

A variety of incubation conditions can be used to form the peptide of the present invention. The most preferred conditions are those which mimic physiological conditions.

E. Construction and Identification of Antibodies.

E.1. Generation and Identification of Antibodies.

The proteins of the present invention can be used in a variety of procedures and methods, such as for the generation of antibodies, for use in identifying pharmaceutical compositions, and for studying DNA/protein interaction.

In one embodiment, the protein is used as an immunogen to generate an antibody which is capable of binding to the kinase, preferably to IT-11. In a further aspect of this embodiment, the antibody is additionally incapable of binding to the individual subunit even though it binds to the kinase, preferably IT-11.

The peptide of the present invention, preferably IT-11, can be used to produce antibodies or hybridomas. One skilled in the art will recognize that if an antibody is desired that will bind to the kinase, such a peptide would be generated as described above and used as an immunogen. The resulting antibodies are then screened for the ability to bind the kinase. Additionally, the antibody can be screened for an inability to bind the kinase.

The antibodies of the present invention include monoclonal and polyclonal antibodies, as well fragments of these antibodies, and humanized forms. Humanized forms of the antibodies of the present invention may be generated using one of the procedures known in the art such as chimerization or CDR grafting.

The invention also provides hybridomas which are capable of producing the above-described antibodies. A hybridoma is an immortalized cell line which is capable of secreting a specific monoclonal antibody.

In general, techniques for preparing monoclonal antibodies and hybridomas are well known in the art (Campbell, "Monoclonal Antibody Technology: Laboratory Techniques in Biochemistry and Molecular Biology," Elsevier Science Publishers, Amsterdam, The Netherlands (1984); St. Groth et al., J. Immunol. Methods 35:1-21 (1980)).

Any animal (mouse, rabbit, and the like) which is known to produce antibodies can be immunized with the selected polypeptide. Methods for immunization are well known in the art. Such methods include subcutaneous or interperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or $\beta$-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., Exp. Cell Res. 175:109-124 (1988)).

Hybridomas secreting the desired antibodies are cloned and the class and subclass is determined using procedures known in the art (Campbell, Monoclonal Antibody Technology: Laboratory Techniques in Biochemistry and Molecular Biology, supra (1984)).

For polyclonal antibodies, antibody containing antisera is isolated from the immunized animal and is screened for the presence of antibodies with the desired specificity using one of the above-described procedures.

In another embodiment of the present invention, the above-described antibodies are detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Sternberger et al., J. Histochem. Cytochem. 18:315 (1970); Bayer et al., Meth. Enzym. 62:308 (1979); Engval et al., Immunol. 109:129 (1972); Goding, J. Immunol. Meth. 13:215 (1976)). The labeled antibodies of the present invention can be used for in vitro, in vivo, and in situ assays to identify cells or tissues which express a specific peptide.

In another embodiment of the present invention the above-described antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10 (1986); Jacoby et al., Meth. Enzym. 34 Academic Press, N.Y. (1974)). The immobilized antibodies of the present invention can be used for in vitro, in vivo, and in situ assays as well as in immunochromotography.

E.2. Methods of Determining Expression With Antibodies.

In another embodiment of the present invention, methods of determining the expression of a specific kinase in a test sample are presented. In detail, the methods comprise incubating a test sample with one or more of the antibodies of the present invention and assaying whether the antibody binds to the test sample.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, "An Introduction to Radioimmunoassay and Related Techniques" Elsevier Science Publishers, Amsterdam, The Netherlands (1986); Bullock et al., "Techniques in Immunocytochemistry," Academic Press, Orlando, Fla. Vol. 1 (1982), Vol. 2 (1983), Vol. 3 (1985); Tijssen, "Practice and Theory of Enzyme Immunoassays: Laboratory Techniques in Biochemistry and Molecular Biology," Elsevier Science Publishers, Amsterdam, The Netherlands (1985).

The immunological assay test samples of the present invention include cells, protein or membrane extracts of cells, or biological fluids, such as blood, serum, plasma, urine, or the like. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

F. Detection Kits.

In another embodiment of the present invention, a kit is provided which contains all the necessary reagents to carry out the previously described methods of detection.

F.1. Kits Comprising Nucleic Acid Printers or Probes.

Specifically, the invention provides a kit compartmentalized to receive in close confinement one or more containers which comprises: a) a first container comprising a nucleic acid probe capable of hybridizing to a nucleic acid sequence encoding a mammalian G protein-coupled receptor kinase; and b) one or more other containers comprising one or more of the following: wash reagents and reagents capable of detecting the presence of bound nucleic acid probe from the first container. Preferably, the nucleic acid sequence encodes IT-11.

The invention further provides a kit compartmentalized to receive in close confinement one or more containers which comprises: a) a first container comprising a nucleic acid probe capable of hybridizing to nucleic acid sequences encoding a gene from the Huntington's disease region of chromosome 4; and b) one or more other containers comprising one or more of the following: wash reagents and reagents capable of detecting the presence of bound nucleic acid probe from the first container. Preferably, the nucleic acid sequence encodes IT-11.

In addition, the invention provides a compartmentalized kit to receive in close confinement, one or more containers which comprises: (a) a first container comprising one or more of the amplification primers of the present invention; and (b) one or more other containers comprising one or more of the following: a sample reservoir, wash reagents, or reagents capable of amplifying sequences hybridizing to the amplification primers.

F.2. Kits Comprising Antibodies.

The invention further provides a kit compartmentalized to received in close confinement one or more containers which comprises: a) a first container comprising an antibody capable of binding to a mammalian G protein-coupled receptor kinase; and b) one or more other containers comprising one or more of the following: wash reagents and reagents capable of detecting the presence of bound antibodies from the first container. Preferably, the antibody is capable of binding to IT-11.

The invention also provides a compartmentalized kit to receive, in close confinement, one or more containers which comprises: a) a first container comprising an antibody capable of binding to the expression product of a gene from the Huntington's disease region of chromosome 4; and b) one or more other containers comprising one or more of the following: wash reagents and reagents capable of detecting the presence of bound antibodies from the first container. Preferably, the antibody is capable of binding to IT-11.

F.3. Kit Components.

The materials for use in the invention are ideally suited for the preparation of a kit. In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like.

Types of detection reagents include labeled secondary probes, or in the alternative, if the primary probe is labeled, the enzymatic, or antibody binding reagents which are capable of reacting with the labeled probe. One skilled in the art will readily recognize that the disclosed probes and amplification primers of the present invention can readily be incorporated into one of the established kit formats which are well known in the art.

For antibodies, examples of detection reagents include, but are not limited to, labeled secondary antibodies, or in the alternative, if the primary antibody is labeled, the chromophoric, enzymatic, or antibody binding reagents which are capable of reacting with the labeled antibody. For nucleic acid probes, examples of detection reagents include, but are not limited to radiolabeled probes, enzymatic labeled probes (horse radish peroxidase, alkaline phosphatase), and affinity labeled probes (biotin, avidin, or steptavidin). One skilled in the art will readily recognize that the antibodies and nucleic acid probes described in the present invention can readily be incorporated into one of the established kit formats which are well known in the art.

G. Anti-peptide Antibodies.

In another embodiment, the peptide, in particular the IT-11 peptide, is used to generate an antibody which is capable of binding to the peptide (e.g., anti-IT-11 peptide antibodies). The anti-peptide antibodies of the present invention may include monoclonal and polyclonal antibodies, as well fragments of these antibodies, and humanized forms. Humanized forms of the antibodies of the present invention may be generated using one of the procedures known in the art such as chimerization or CDR grafting.

Moreover, the invention also provides hybridomas which are capable of producing the above-described antibodies.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In *Synthetic Peptides, A User's Guide,* W. H. Freeman, N.Y., pp. 289–307 (1992), and Kaspczak et al., *Biochemistry* 28:9230-8 (1989).

Anti-peptide peptides can be generated in one of two fashions. First, the anti-peptide peptides can be generated by replacing the basic amino acid residues found in the peptide sequence, e.g., the IT-11 peptide sequence, with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

Alternatively, the anti-peptide peptides of the present invention can be generated by synthesizing and expressing a peptide encoded by the antisense strand of the DNA which encodes the peptides, preferably the IT-11 peptide. Peptides produced in this fashion are, in general, similar to those described above since codons complementary to those coding for basic residues generally code for acidic residues.

H. Methods for Decreasing Peptide Expression and Activity.

In another embodiment of the present invention, methods for decreasing the activity of the G protein-coupled receptor kinase can be modulated by providing an agent capable of binding to the peptide. Such agents include, but are not limited to, the anti-kinase antibodies and the antipeptide peptides of the present invention. By decreasing the activity of the G protein-coupled receptor kinase, the effects which the expression of the peptide has on the activation of Huntington's disease may be decreased.

In another embodiment of the present invention, methods are presented for decreasing the expression of the peptide disclosed herein, preferably IT-11 peptide. Specifically, anti-sense RNA expression is used to disrupt the translation of the genetic message.

In detail, a cell is modified using routine procedures such that it expresses an antisense message, a message which is complementary to the IT-11 message. By constitutively or inducibly expressing the antisense RNA, the translation of IT-11 mRNA can be regulated.

All essential publications mentioned hereinabove are hereby incorporated in their entirety by reference.

In order that those skilled in the art can more fully understand this invention the following examples are set forth. These examples are given solely for the purpose of illustration, and should not be considered as expressing limitations unless so set forth in the appended claims.

EXAMPLES

In the following examples and protocols, restriction enzymes, ligase, and all commercially available reagents were utilized in accordance with the manufacturer's recommendations. Standard methods and techniques for cloning and molecular analysis, as well as the preparation of standard reagents were performed essentially in accordance with *Molecular Cloning: A Laboratory Manual, second edition*, edited by Sambrook, Fritsch & Maniatis, Cold Spring Harbor Laboratory, 1989).

EXAMPLE 1

Cosmid Clones and Exon Amplification

The exon amplification procedure described by Buckler et al. (*Proc. Natl. Acad. Sci. U.S.A.* 88:4005–4009 (1991)) was used to isolate coding sequences from cosmid BJ56 (Allitto et al., *Genomics* 9:104–112 (1991)), and to the overlapping cosmid 21C5. The two cosmids were selected because of their locus in the proximal portion of 4p16.3 in the same physical region as D4S10, and because of the high level of linkage disequilibrium with Huntington's disease displayed by polymorphisms across this region (MacDonald et al., *Nature Genet.* 1:99–103 (1992)).

The small fragments of the cosmids were then subcloned into the pSPL1 vector and used to transfect cos7 cells. Subsequently, PCR amplification was applied to first strand cDNA made from the resultant cos7 cell mRNA. Then the PCR products were subcloned into "T"-tailed EcoRV digested pBSKII vector (Stratagent) (Marchuk et al., *Nucl. Acids Res.* 19:1154 (1991)). Sequencing of the cDNA subclones revealed two exons, d21C5-3A, and dBJ56-3A, of 77 bp and 137 bp, respectively.

EXAMPLE 2

Isolation and Expression of the cDNA Clone IT11-A.

To isolate a gene from within the chromosomal region of the Huntington's disease defect, exon dBJ56-3A was labeled with $^{32}$P-dATP (Feinberg et al., *Anal. Biochem.* 137:266–267 (1984)) and used to screen 1 million clones of an oligo dT primed lambda ZapII human frontal cortex cDNA library. The screen produced a single clone, IT11-A, with an insert of 1.73 kb. To confirm the accuracy of the hybridization, IT11-A was rehybridized to BJ56 and 21C5.

Mapping of IT-11 Within 4p16.3.

To determine the location of IT-11 on the human chromosome, a radioactively labeled 260 bp EcoRI fragment from IT11-A was hybridized to a genomic blot of PstI-digested DNA from the following sources: human neuroblastoma NGP, hamster (UCW104), and several human-hamster hybrid (HHW) cell line strains. The HHW cell line strains used in the regional somatic cell hybrid mapping panel were characterized as follows: hybrid HHW416 contained an intact chromosome 4 as its only human material; HHW661 contained a human translocation chromosome comprised of loci 4pter-4p15.1 and 5p15.1-5cen; HHW599 contained chromosome 5 as its only human material (no chromosome 4 DNA); HHW847 contained a t(4;21) translocation that deleted all of locus 4p16.3; HHW842 contained the telomeric 2 Mb of locus 4p16.3, but was missing the proximal portion of the region due to an interstitial deletion; and HHW1071 contained a t(4;12) translocation that retained about 3 Mb at the telomere of 4p. The DNA probe hybridized to 3.4 kb and 1.0 kb fragments that mapped to a 1.2 Mb central region of 4p16.3, that was present in cell hybrid HHW1071, but absent from both HHW842 and HHW847. The Pst site in genomic DNA is spanned by the IT-11 cDNA probe sequence.

As shown in FIG. 1, a partial long range restriction map adapted from Lin et al., *Somat. Cell Mol. Genet.* 17:481–488 (1991), was determined for 4p16.3. The Huntington's disease region, as indicated in FIG. 1, has been disclosed by MacDonald et al., *Neuron* 3:183–190 (1989); Bates et al., *Am. J. Hum. Genet.* 49:7–16 (1991); Gusella, *Adv. Hum. Genet.* 20:125–151 (1991); and Snell et al., *Am. J. Hum. Genet.* 51:357–362 (1992). Regions of 4p16.3 were present in cell hybrids HHW1071, HHW842, HHW416, and HHW661, but absent from both HHW599 and HHW847. Thus, the hybrid breakpoints subdivided the Huntington's disease region of the chromosome into three segments. IT-11 was digested with restriction enzymes Not I, Mlu I and Nru I to establish the restriction map. As indicated in FIG. 1, sites indicated in boldface type displayed complete digestion, whereas sites indicated in lighter symbols, frequently were incompletely digested. The frequent incomplete digestion was probably due to partial methylation. Additional clustered Not I sites were found between D4S114 and D4S186.

EXAMPLE 3

Characterization of IT-11

DNA Comparison.

A Southern blot assay was used to map physical rearrangements in or near the DNA sequence coding for IT-11 in individuals with Huntington's disease. For the comparison, DNA was isolated from seven individuals:

two normal controls, two adult-onset individuals who were heterozygous for Huntington's disease, one juvenile-onset individual who was heterozygous for Huntington's disease and two independent individuals who were homozygous for Huntington's disease. The DNA was digested using eight different restriction enzymes: BamHI, HindIII, EcoRI, PstI, RsaI, Sau96A, HinfI and HaeIII, according to the method of hybridization exemplified by Gusella et al., Nature 306:234–238 (1983).

Although no differences in restriction fragment size were detected, the assay was sufficiently sensitive only to indicate gross morphology of the sequence, not minor changes. However, it is recognized that even minor perturbations of the sequence could result in the slow, progressive neuronal death of Huntington's disease.

Isolation of RNA and Northern Analysis.

To determine the tissue distribution of IT-11, a northern blot analysis was conducted using RNA from normal individuals and from individuals with Huntington's disease. Total R. NA was isolated from cultured human lymphoblasts and human and baboon tissues (brain regions, liver, kidney, spleen, heart, adrenal, muscle and testis) by the guanidium isothiocyanate/CsCl gradient procedure. All lanes were loaded with 30 ug of total RNA that displayed intact 18S and 28S ribosomal RNA bands at the positions indicated. Then the RNA was denatured in formamide and electrophoresed on 1.2% 6M formaldehyde agarose gels (Maniatis et al., *Molecular Cloning (A Laboratory Manual)*, Cold Spring Harbor Laboratory, second edition (1982)). The gels were stained in ethidium bromide to visualize the ribosomal RNA bands. Then the gels were northern blotted onto nylon membrane (Hybond N, Amersham) in 20XSSC.

A 1 kb EcoRI fragment of IT 11-A was used to probe the northern blots of RNA from the various baboon tissues to estimate the size of the corresponding mRNA, and its distribution. Hybridization of the northern blots with $^{32}$P-labeled DNA probes was carried out as described by Taylor et al., *Hum. Mol. Genet.* 1:142 (1992).

Analysis of the northern blot revealed a single mRNA of about 2.5 kb in the sample from baboon testis. However, the mRNA in the remaining tested tissues, including human frontal cortex, hybridized to the probe at levels below the measurable detection of the assay. The higher level of mRNA expression in testis, suggested an abundance of the target receptor in this tissue.

Similarly, a northern blot using normal cells and homozygote lymphoblasts from Huntington's disease patients was used to assess whether Huntington's disease was associated with an increase in the level of expression of the IT-11 sequence. The hybridization was again as described by Taylor et al., in press (1992). However, as above, the corresponding mRNA was below detectable levels in the RNA's from both the normal individuals and those with Huntington's disease.

PCR Analysis of Human Expression.

Since neither human testis RNA nor an equivalent cDNA library were available to the inventors, PCR analysis of a 91 bp fragment of IT-11 was used to determine whether clones could be detected in libraries from other tissues despite the absence of detectable signal on the northern blots. The following human cDNA libraries were tested: adenovirus transformed retinal cell, fetal liver, adult liver, adult frontal cortex, fetal brain, fetal retina, fetal spleen, sciatic nerve and lymphoblast.

The analysis was performed as described in Ambrose et al., *Hum. Mol. Gen.* 1 (1992).

The appropriate sized PCR product was detected in each library tested. Moreover, a reaction in which no cDNA library template was added failed to yield an amplification product. Thus, although not apparent from the previous northern blot, these results suggested that the IT-11 sequence is expressed at low levels in many adult and fetal tissues. Further this suggested that since the kinase is also expressed widely in other tissues, including the brain cortex and striatum, at least some expression of the associated receptor is also likely in these areas.

EXAMPLE 4

Sequence of IT-11

Extension to the 5'-End of the IT-11 Gene.

To extend the IT-11 sequence more 5', an additional $10^6$ randomly-primed lambda ZapI cDNAs from an adenovirus transformed human retinal cell line (RIC2) were screened using the predicted 5' portion of IT11-A (a 260 bp EcoRI fragment). As shown in FIG. 2A to 2C, this screen produced two additional clones, IT11-B and IT11-C. Both extended approximately 150 bp in the 5' direction from the IT11-A sequence.

Sequencing of IT-11.

The cDNA clones, IT11-A, IT11-B and IT11-C, and trapped exons were sequenced by the dideoxy chain termination method (Sanger et al., *Proc. Natl. Acad. Sci. U.S.A.* 74:5463–5467 (1977)) using Sequenase TM enzyme and reagents supplied by the manufacturer in the deaza-dGTP Sequencing Kit (USB). Oligonucleotides for sequencing and the PCR were synthesized using an automated DNA synthesizer (Biosearch). Cosmid DNAs were sequenced directly using the Sequenase TM, deazad GTP Sequencing Kit (USB) as described by McClatchey et al., *Hum. Mol. Genet.*, in press (1992).

The composite DNA sequence, IT-11, comprised of IT11-A, -B and -C was determined to contain 1886 bp, as shown in FIG. 2A to 2C. Specifically, IT11-A was found to span bases 156–1886, and the 5' extension was derived from the overlapping clones IT11-B and -C which spanned bases 1–306 and 34–306, respectively. The composite DNA sequence, SEQ ID NO:1, has been placed in GENBANK (accession number L03718).

As also shown in FIG. 2A to 2C, an open reading frame of 1500 bp was identified within the 1886 bp sequence, beginning at the putative initiator methionine at base 255. Furthermore, it was determined that this ATG codon was preceded by a translation initiation sequence, and a GC-rich upstream segment that contained no stop codons. In addition, the 3' end of the sequence was found to contain two potential poly(A) addition signals (AATAAA) at positions 43 bp and 29 bp upstream from a short poly(A) tail.

The predicted protein product, SEQ ID NO. 2, of the characteristic kinase domain comprises 500 amino acids ending with a putative stop codon, as shown in FIG. 2A to 2C. In addition, both trapped exons, dBJ56-3 and d21C5, were found in the disclosed sequence of IT-11 as also shown in FIG. 2.

EXAMPLE 5

Alignment of the Predicted IT-11 Protein With Related G Protein-Coupled Receptor Kinase The composite IT-11 sequence was used to search for similarities in GENBANK using the BLAST network service of the National Center for Biotechnology Information (Altschul et al., *J. Mol. Biol.* 217:403–410 (1990)), and the PILEUP - GCG sequence analysis package (Devereux et al., *Nucl. Acids Res.* 12:387–395 (1984)). The IT-11 protein was aligned with Gprk-2, Drosophila G protein-coupled receptor kinase-2 (Cassill et al., *Proc. Natl. Acad. Sci. U.S.A.* 88:11067–11070 (1991)); RHKIN, bovine rhodopsin kinase (Lorenz et al., *Proc. Natl. Acad. Sci. U.S.A.* 88:8715–8719 (1991)); Gprk-1, Drosophila G protein-coupled receptor kinase-1 (Cassill et al., *Proc. Natl. Acad. Sci. U.S.A.* 88:11067–11070 (1991)); and βARK-1, human β adrenergic receptor kinase-1 (Benovic et al., *FEBS Lett.* 283:122–126 (1991)).

This analysis revealed that IT-11 encodes a novel member of a family G protein-coupled receptor kinases that is typified by rhodopsin kinase and the β-adrenergic receptor kinase. Similar results were obtained with the highly related bovine and rat β adrenergic receptor kinases.

The sequence most closely related to IT-11 is a Drosophila G protein-coupled receptor kinase encoded by locus Gprk-2 ($P<2.7e^{-152}$ based on BLASTX) which shows 83% amino acid identity (over 372 aa), and 60% nucleic acid identity across the coding region (Cassill et al., *Proc. Natl. Acad. Sci. U.S.A.* 88:11067–11070 (1991)). The amino acid similarity between the Gprk-2 kinase and the predicted IT-11 product was found to end abruptly at the N-terminus of Gprk-2, corresponding to residue 134 of IT-11.

Upon analysis, other members of this family showed somewhat less similarity to IT-11 than Drosophila Gprk-2. Bovine rhodopsin kinase was found to have 48% amino acid identity; Drosophila Gprk-1 was found to have 39% identity; and human βARK was found to have 38% identity. However, in a comparison with both Drosophila Gprk-1 and human βARK, their relatedness to IT-11 extended to the N-terminus. Nevertheless, IT-11 contained a prominent gap relative to the both Drosophila Gprk-1 and human βARK proteins after residue 23.

The GC-rich 5' untranslated sequence of IT-11 was also found to contain several direct CGG repeats that show similarity ($P=0.00016$ using BLASTN) with the sequence at the FMR locus that undergoes expansion in fragile X-associated mental retardation (Verkerk et al., *Cell* 65:905–914 (1991)).

EXAMPLE 6

Single-Strand Conformational Polymorphism

To scan for sequence differences between Huntington's disease and normal individuals, a comparison was made between 200 bp stretches across the entire cloned IT-11 sequence, using the SSCP (single strand conformational polymorphisms) technique (Orita et al., *Genomics* 5:874–879 (1989)). The SSCP pattern was determined by comparing an undenatured and denatured amplified 91 bp PCR product from IT11-A and three independent cosmids from the corresponding locus: BJ56, BJ56W4 and 20G3.

The PCR reactions were carried out using each of the following as templates: oligo-dT-primed first strand cDNA made from total RNA of normal and Huntington's disease lymphoblasts; 1 pg of cosmid DNA; or 5 ng of genomic DNA front normal or Huntington's disease lymphoblasts. The reactions contained two unlabeled primers, SEQ ID NOS:3 and 4, respectively, 5'GATCCTCATGCCGTTTAC3' and 5'AAGTCTTCATCTGCGGTG3' (100 ng), all four dNTPs, and one μl of (alpha-$^{32}$P) dATP or cDTP (3000 Ci/mmol, 10 mCi/Ml; Amersham). One μl of the labeled PCR product was then diluted 1:100 in water and 3 μl of this mixture were added to an equal volume of stop mix (USB Sequenase ™ kit) and heated to 94° C. for 5 min. The samples were electrophoresed through a 6% polyacrylamide gel containing 8% glycerol at room temperature for 126 hr at 7 W (Orita et al., *Genomics* 5:874–879 (1989)). The gel was dried and exposed to XAR film (Kodak) with an intensifying screen (Dupont Cronex).

An evaluation of the SSCP scan revealed a single variation within bp 1563–1654. The gel showed that IT11-A and BJ56 displayed fragments in the denatured product lane characteristic of allele A2, corresponding to an ALA codon, while the remaining two cosmids, BJ56W4 and 20G3, produced fragments characteristic of allele A1, corresponding to the alternate VAL codon.

The presence of the codon variation was confirmed in each case by DNA sequence analysis. To identify the precise sequence difference, the same PCR primers were used to directly sequence this region of cosmids from independent chromosomes. The comparison revealed a C to T transition in codon 454 that changed ALA to VAL.

Such a change in amino acid sequence is a common polymorphism having allele frequencies on normal chromosomes (N-162) of 54% and 46% for ALA and VAL, respectively. Moreover, this polymorphism displayed a significant linkage disequilibrium with Huntington's disease, (77% ALA, 23% VAL, N-48; $X^2-7.8$, $P<0.005$), which was not surprising considering its location within the D4S180–D4S182 region that displays a conserved haplotype on about one-third of Huntington's disease chromosomes.

In addition, a comparison was made between the 5' 300 bp and the 3' 180 bp fragments by direct sequence analysis in Huntington's disease and normal cosmids. The sequence analysis revealed no difference between the cosmids.

Although the present invention has been described with reference to the presently preferred embodiments, the skilled artisan will appreciate that various modifications, substitutions, omissions, and changes may be made without departing from the spirit of the invention. Accordingly, it is intended that the scope of the present invention be limited only by the scope of the following claims, including equivalents thereof.

What is claimed is:

1. An isolated DNA segment encoding IT-11, wherein IT-11 comprises the amino acid sequence set forth in SEQ ID NO:2.

2. The DNA segment according to claim 1, wherein the DNA segment comprises the nucleic acid sequence set forth in SEQ ID NO:1.

3. The DNA segment according to claim 1, wherein the DNA segment comprises the nucleic acid sequence set forth in SEQ ID NO:1 which encodes the amino acid sequence set forth in SEQ ID NO:2.

4. A recombinant DNA molecule comprising, 5' to 3', a promoter effective to initiate transcription in a host cell and the encoding sequence according to claim 1.

5. A recombinant DNA molecule comprising a vector and the DNA segment according to claim 1.

6. A host cell comprised of the recombinant DNA molecule according to claim 28.

7. A nucleic acid probe for the detection of a G protein-coupled receptor kinase comprising a nucleic acid fragment capable of specifically hybridizing to the DNA segment according to claim 1, wherein said probe comprises 18 contiguous nucleotides of the sequence according to SEQ ID NO:1 or its complement.

8. A nucleic acid probe for the detection of Huntington's disease in a patient comprising a nucleic acid fragment capable of specifically hybridizing to the DNA segment according to claim 1, wherein said probe comprises 18 contiguous nucleotides of the sequence according to SEQ ID NO:1 or its complement.

9. A kit for amplifying a gene, or fragment thereof, encoding a G protein-coupled receptor kinase, comprising a nucleic acid probe according to claim 7.

10. A DNA construct comprising a transcriptional control region functional in a host cell, a sequence wherein the sequence is complimentary to an RNA sequence of IT-11 on a strand used for expression, and a transcriptional termination region functional in the host cell.

11. A host cell comprising a DNA construct according to claim 10.

* * * * *

UNITED STATES PATENT AND TRADEMARK OFFICE
CERTIFICATE OF CORRECTION

PATENT NO. : 5,366,889
DATED : November 22, 1994
INVENTOR(S) : MacDonald et al.

It is certified that error appears in the above-indentified patent and that said Letters Patent is hereby corrected as shown below:

Column 35, line 56, claim 6, change "Claim 28" to --Claim 5--.

Signed and Sealed this

Twenty-first Day of March, 1995

*Attest:*

BRUCE LEHMAN

*Attesting Officer*   *Commissioner of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
    ( A ) LENGTH: 1886 base pairs
    ( B ) TYPE: nucleic acid
    ( C ) STRANDEDNESS: both
    ( D ) TOPOLOGY: both ( i x ) FEATURE:
    ( A ) NAME/KEY: CDS
    ( B ) LOCATION: 255..1757

( x i ) SEQUENCE DESCRIPTION: SEQ ID NO:1:

```
GCAGCCGCCG CGGTCGGGCT GCCCCCTCCC CTCGCCCCGA CCGCTCCCCT GCTGGTGAGG         60

GCCTGCGCAG GCGGCGGCGG CGGCGCCCTT GGTGGCAGTG GTGGCGGCGG AGCAGCCTCC        120

CGGGATCGTG TCTGGAGCTC GAGGAGAGGG TAGTGCCCGG CGAGCTATGC ACGGGGGCGG        180

CGGCGTCTCC TCCTGTTCCG CCTCCTCAGT CTCCTCGGTC TCGCAGAATC CGCCGGCGGC        240

GGCGGCGCCA GGAC ATG GAG CTC GAG AAC ATC GTG GCC AAC TCG CTG CTG         290
              Met Glu Leu Glu Asn Ile Val Ala Asn Ser Leu Leu
                1           5                  10

CTG AAA GCG CGT CAA GAA AAG GAT TAT AGC AGT CTT TGT GAC AAG CAA         338
Leu Lys Ala Arg Gln Glu Lys Asp Tyr Ser Ser Leu Cys Asp Lys Gln
         15                  20                  25

CCG ATA GGA AGA CGT CTC TTC AGG CAG TTC TGT GAT ACC AAA CCC ACT         386
Pro Ile Gly Arg Arg Leu Phe Arg Gln Phe Cys Asp Thr Lys Pro Thr
     30                  35                  40

CTA AAG AGG CAC ATT GAA TTC TTG GAT GCA GTG GCA GAA TAT GAA GTT         434
Leu Lys Arg His Ile Glu Phe Leu Asp Ala Val Ala Glu Tyr Glu Val
 45                  50                  55                  60

GCC GAT GAT GAG GAC CGA AGT GAT TGT GGA CTG TCA ATC TTA GAT AGA         482
Ala Asp Asp Glu Asp Arg Ser Asp Cys Gly Leu Ser Ile Leu Asp Arg
                 65                  70                  75

TTC TTC AAT GAT AAG TTG GCA GCC CCT TTA CCA GAA ATA CCT CCA GAT         530
Phe Phe Asn Asp Lys Leu Ala Ala Pro Leu Pro Glu Ile Pro Pro Asp
             80                  85                  90

GTT GTG ACA GAA TGT AGA TTG GGA CTG AAG GAG GAG AAC CCT TCC AAA         578
Val Val Thr Glu Cys Arg Leu Gly Leu Lys Glu Glu Asn Pro Ser Lys
         95                 100                 105

AAA GCC TTT GAG GAA TGT ACT AGA GTT GCC CAT AAC TAC CTA AGA GGG         626
Lys Ala Phe Glu Glu Cys Thr Arg Val Ala His Asn Tyr Leu Arg Gly
     110                 115                 120

GAA CCA TTT GAA GAA TAC CAA GAA AGC TCA TAT TTT TCT CAG TTT TTA         674
Glu Pro Phe Glu Glu Tyr Gln Glu Ser Ser Tyr Phe Ser Gln Phe Leu
125                 130                 135                 140

CAA TGG AAA TGG CTG GAA AGG CAA CCC GTA ACA AAG AAC ACA TTT AGA         722
Gln Trp Lys Trp Leu Glu Arg Gln Pro Val Thr Lys Asn Thr Phe Arg
                145                 150                 155

CAT TAC AGA GTT CTA GGA AAA GGC GGA TTT GGA GAG GTT TGC GCC TGT         770
His Tyr Arg Val Leu Gly Lys Gly Gly Phe Gly Glu Val Cys Ala Cys
            160                 165                 170

CAA GTG CGA GCC ACA GGA AAA ATG TAT GCC TGC AAA AAG CTA CAA AAA         818
Gln Val Arg Ala Thr Gly Lys Met Tyr Ala Cys Lys Lys Leu Gln Lys
        175                 180                 185

AAA AGA ATA AAG AAG AGG AAA GGT GAA GCT ATG GCT CTA AAT GAG AAA         866
Lys Arg Ile Lys Lys Arg Lys Gly Glu Ala Met Ala Leu Asn Glu Lys
    190                 195                 200

AGA ATT CTG GAG AAA GTG CAA AGT AGA TTC GTA GTT AGT TTA GCC TAC         914
Arg Ile Leu Glu Lys Val Gln Ser Arg Phe Val Val Ser Leu Ala Tyr
205                 210                 215                 220

GCT TAT GAA ACC AAA GAT GCC TTG TGC TTG GTG CTC ACC ATT ATG AAT         962
Ala Tyr Glu Thr Lys Asp Ala Leu Cys Leu Val Leu Thr Ile Met Asn
```

```
                            225                            230                           235

GGA  GGG  GAT  TTG  AAG  TTT  CAC  ATT  TAC  AAC  CTG  GGC  AAT  CCC  GGC  TTT          1010
Gly  Gly  Asp  Leu  Lys  Phe  His  Ile  Tyr  Asn  Leu  Gly  Asn  Pro  Gly  Phe
               240                 245                           250

GAT  GAG  CAG  AGA  GCC  GTT  TTC  TAT  GCT  GCA  GAG  CTG  TGT  TGC  GGC  TTG          1058
Asp  Glu  Gln  Arg  Ala  Val  Phe  Tyr  Ala  Ala  Glu  Leu  Cys  Cys  Gly  Leu
          255                      260                      265

GAA  GAT  TTA  CAG  AGG  GAA  AGA  ATT  GTA  TAC  AGA  GAC  TTG  AAG  CCT  GAG          1106
Glu  Asp  Leu  Gln  Arg  Glu  Arg  Ile  Val  Tyr  Arg  Asp  Leu  Lys  Pro  Glu
     270                      275                      280

AAT  ATT  CTC  CTT  GAT  GAT  CGT  GGA  CAC  ATC  CGG  ATT  TCA  GAC  CTC  GGT          1154
Asn  Ile  Leu  Leu  Asp  Asp  Arg  Gly  His  Ile  Arg  Ile  Ser  Asp  Leu  Gly
285                      290                      295                       300

TTG  GCC  ACA  GAG  ATC  CCA  GAA  GGA  CAG  AGG  GTT  CGA  GGA  AGA  GTT  GGA          1202
Leu  Ala  Thr  Glu  Ile  Pro  Glu  Gly  Gln  Arg  Val  Arg  Gly  Arg  Val  Gly
                    305                      310                      315

ACA  GTC  GGC  TAC  ATG  GCA  CCT  GAA  GTT  GTC  AAT  AAT  GAA  AAG  TAT  ACG          1250
Thr  Val  Gly  Tyr  Met  Ala  Pro  Glu  Val  Val  Asn  Asn  Glu  Lys  Tyr  Thr
               320                      325                      330

TTT  AGT  CCC  GAT  TGG  TGG  GGA  CTT  GGC  TGT  CTG  ATC  TAT  GAA  ATG  ATT          1298
Phe  Ser  Pro  Asp  Trp  Trp  Gly  Leu  Gly  Cys  Leu  Ile  Tyr  Glu  Met  Ile
          335                      340                      345

CAG  GGA  CAT  TCT  CCA  TTC  AAA  AAA  TAC  AAA  GAG  AAA  GTC  AAA  TGG  GAG          1346
Gln  Gly  His  Ser  Pro  Phe  Lys  Lys  Tyr  Lys  Glu  Lys  Val  Lys  Trp  Glu
     350                      355                      360

GAG  GTC  GAT  CAA  AGA  ATC  AAG  AAT  GAT  ACC  GAG  GAG  TAT  TCT  GAG  AAG          1394
Glu  Val  Asp  Gln  Arg  Ile  Lys  Asn  Asp  Thr  Glu  Glu  Tyr  Ser  Glu  Lys
365                      370                      375                       380

TTT  TCA  GAG  GAT  GCC  AAA  TCT  ATC  TGC  AGG  ATG  TTA  CTC  ACC  AAG  AAT          1442
Phe  Ser  Glu  Asp  Ala  Lys  Ser  Ile  Cys  Arg  Met  Leu  Leu  Thr  Lys  Asn
                    385                      390                      395

CCA  AGC  AAG  CGG  CTG  GGC  TGC  AGG  GGC  GAG  GGA  GCG  GCT  GGG  GTG  AAG          1490
Pro  Ser  Lys  Arg  Leu  Gly  Cys  Arg  Gly  Glu  Gly  Ala  Ala  Gly  Val  Lys
               400                      405                      410

CAG  CAC  CCC  GTG  TTC  AAG  GAC  ATC  AAC  TTC  AGG  AGG  CTG  GAG  GCA  AAC          1538
Gln  His  Pro  Val  Phe  Lys  Asp  Ile  Asn  Phe  Arg  Arg  Leu  Glu  Ala  Asn
          415                      420                      425

ATG  CTG  GAG  CCC  CCT  TTC  TGT  CCT  GAT  CCT  CAT  GCC  GTT  TAC  TGT  AAG          1586
Met  Leu  Glu  Pro  Pro  Phe  Cys  Pro  Asp  Pro  His  Ala  Val  Tyr  Cys  Lys
     430                      435                      440

GAC  GTC  CTG  GAT  ATC  GAG  CAG  TTC  TCG  GCG  GTG  AAA  GGG  ATC  TAC  CTG          1634
Asp  Val  Leu  Asp  Ile  Glu  Gln  Phe  Ser  Ala  Val  Lys  Gly  Ile  Tyr  Leu
445                      450                      455                       460

GAC  ACC  GCA  GAT  GAA  GAC  TTC  TAT  GCT  CGG  TTT  GCT  ACC  GGG  TGT  GTC          1682
Asp  Thr  Ala  Asp  Glu  Asp  Phe  Tyr  Ala  Arg  Phe  Ala  Thr  Gly  Cys  Val
                    465                      470                      475

TCC  ATC  CCC  TGG  CAG  AAT  GAG  GAC  TGC  CTG  ACC  ATG  GTC  CCC  AGT  GAG          1730
Ser  Ile  Pro  Trp  Gln  Asn  Glu  Asp  Cys  Leu  Thr  Met  Val  Pro  Ser  Glu
               480                      485                      490

AAG  GAA  GTG  GAA  CCC  AAG  CAA  TGC  TGAGCACCCC  GGTGCGGACC  ACAGAGCAGA              1784
Lys  Glu  Val  Glu  Pro  Lys  Gln  Cys
     495                      500

CCCTGGCGCC  AGGAAGGAGC  ATGTGTTAGC  GTCTCGTCCC  ACCTGGAATT  GTAATAAATA                  1844

CATCTAAATA  AACATGCCT  TGGGAGTGTA  CAGACAAAAA  AA                                        1886
```

( 2 ) INFORMATION FOR SEQ ID NO:2:

( i ) SEQUENCE CHARACTERISTICS:
        ( A ) LENGTH: 500 amino acids
        ( B ) TYPE: amino acid
        ( D ) TOPOLOGY: linear 5,366,889

-continued ( i i ) MOLECULE TYPE: protein ( x i ) SEQUENCE DESCRIPTION: SEQ ID NO:2:

```
Met Glu Leu Glu Asn Ile Val Ala Asn Ser Leu Leu Leu Lys Ala Arg
 1               5                  10                  15

Gln Glu Lys Asp Tyr Ser Ser Leu Cys Asp Lys Gln Pro Ile Gly Arg
            20                  25                  30

Arg Leu Phe Arg Gln Phe Cys Asp Thr Lys Pro Thr Leu Lys Arg His
        35                  40                  45

Ile Glu Phe Leu Asp Ala Val Ala Glu Tyr Glu Val Ala Asp Asp Glu
    50                  55                  60

Asp Arg Ser Asp Cys Gly Leu Ser Ile Leu Asp Arg Phe Phe Asn Asp
65                  70                  75                  80

Lys Leu Ala Ala Pro Leu Pro Glu Ile Pro Pro Asp Val Val Thr Glu
                85                  90                  95

Cys Arg Leu Gly Leu Lys Glu Glu Asn Pro Ser Lys Lys Ala Phe Glu
            100                 105                 110

Glu Cys Thr Arg Val Ala His Asn Tyr Leu Arg Gly Glu Pro Phe Glu
            115                 120                 125

Glu Tyr Gln Glu Ser Ser Tyr Phe Ser Gln Phe Leu Gln Trp Lys Trp
    130                 135                 140

Leu Glu Arg Gln Pro Val Thr Lys Asn Thr Phe Arg His Tyr Arg Val
145                 150                 155                 160

Leu Gly Lys Gly Gly Phe Gly Glu Val Cys Ala Cys Gln Val Arg Ala
                165                 170                 175

Thr Gly Lys Met Tyr Ala Cys Lys Lys Leu Gln Lys Lys Arg Ile Lys
            180                 185                 190

Lys Arg Lys Gly Glu Ala Met Ala Leu Asn Glu Lys Arg Ile Leu Glu
            195                 200                 205

Lys Val Gln Ser Arg Phe Val Val Ser Leu Ala Tyr Ala Tyr Glu Thr
    210                 215                 220

Lys Asp Ala Leu Cys Leu Val Leu Thr Ile Met Asn Gly Gly Asp Leu
225                 230                 235                 240

Lys Phe His Ile Tyr Asn Leu Gly Asn Pro Gly Phe Asp Glu Gln Arg
                245                 250                 255

Ala Val Phe Tyr Ala Ala Glu Leu Cys Cys Gly Leu Glu Asp Leu Gln
            260                 265                 270

Arg Glu Arg Ile Val Tyr Arg Asp Leu Lys Pro Glu Asn Ile Leu Leu
            275                 280                 285

Asp Asp Arg Gly His Ile Arg Ile Ser Asp Leu Gly Leu Ala Thr Glu
    290                 295                 300

Ile Pro Glu Gly Gln Arg Val Arg Gly Arg Val Gly Thr Val Gly Tyr
305                 310                 315                 320

Met Ala Pro Glu Val Val Asn Asn Glu Lys Tyr Thr Phe Ser Pro Asp
                325                 330                 335

Trp Trp Gly Leu Gly Cys Leu Ile Tyr Glu Met Ile Gln Gly His Ser
            340                 345                 350

Pro Phe Lys Lys Tyr Lys Glu Lys Val Lys Trp Glu Glu Val Asp Gln
            355                 360                 365

Arg Ile Lys Asn Asp Thr Glu Glu Tyr Ser Glu Lys Phe Ser Glu Asp
    370                 375                 380

Ala Lys Ser Ile Cys Arg Met Leu Leu Thr Lys Asn Pro Ser Lys Arg
385                 390                 395                 400

Leu Gly Cys Arg Gly Glu Gly Ala Ala Gly Val Lys Gln His Pro Val
                405                 410                 415
```

```
Phe Lys Asp Ile Asn Phe Arg Arg Leu Glu Ala Asn Met Leu Glu Pro
            420             425                 430

Pro Phe Cys Pro Asp Pro His Ala Val Tyr Cys Lys Asp Val Leu Asp
        435             440                 445

Ile Glu Gln Phe Ser Ala Val Lys Gly Ile Tyr Leu Asp Thr Ala Asp
    450             455                 460

Glu Asp Phe Tyr Ala Arg Phe Ala Thr Gly Cys Val Ser Ile Pro Trp
465                 470                 475                 480

Gln Asn Glu Asp Cys Leu Thr Met Val Pro Ser Glu Lys Glu Val Glu
            485                 490                 495

Pro Lys Gln Cys
            500
```

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: both
        ( D ) TOPOLOGY: both ( x i ) SEQUENCE DESCRIPTION: SEQ ID NO:3:

GATCCTCATG CCGTTTAC                                18

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: both
        ( D ) TOPOLOGY: both ( x i ) SEQUENCE DESCRIPTION: SEQ ID NO:4:

AAGTCTTCAT CTGCGGTG                                18